US009616151B2

(12) United States Patent
Hanson et al.

(10) Patent No.: US 9,616,151 B2
(45) Date of Patent: Apr. 11, 2017

(54) SULFHYDRYL-FUNCTIONALIZED POLYMERIC COMPOSITIONS FOR MEDICAL DEVICES

(71) Applicant: KCI Licensing, Inc., San Antonio, TX (US)

(72) Inventors: Douglas Philip Hanson, San Antonio, TX (US); James Courage, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 39 days.

(21) Appl. No.: 14/438,493

(22) PCT Filed: Oct. 24, 2013

(86) PCT No.: PCT/US2013/066683
§ 371 (c)(1),
(2) Date: Apr. 24, 2015

(87) PCT Pub. No.: WO2014/066684
PCT Pub. Date: May 1, 2014

(65) Prior Publication Data
US 2015/0265743 A1 Sep. 24, 2015

Related U.S. Application Data

(60) Provisional application No. 61/718,130, filed on Oct. 24, 2012.

(51) Int. Cl.
| | |
|---|---|
| *A61L 26/00* | (2006.01) |
| *A61L 15/26* | (2006.01) |
| *A61L 15/42* | (2006.01) |
| *C08G 18/50* | (2006.01) |
| *C08G 18/83* | (2006.01) |
| *C08G 18/38* | (2006.01) |
| *A61F 13/00* | (2006.01) |
| *A61M 1/00* | (2006.01) |
| *C08G 101/00* | (2006.01) |
| *A61N 1/04* | (2006.01) |

(52) U.S. Cl.
CPC .... *A61L 26/0019* (2013.01); *A61F 13/00068* (2013.01); *A61L 15/26* (2013.01); *A61L 15/425* (2013.01); *A61L 26/0066* (2013.01); *A61L 26/0085* (2013.01); *A61M 1/0088* (2013.01); *C08G 18/3876* (2013.01); *C08G 18/3893* (2013.01); *C08G 18/5072* (2013.01); *C08G 18/834* (2013.01); *C08G 18/837* (2013.01); *A61F 2013/00174* (2013.01); *A61L 2300/252* (2013.01); *A61N 1/0412* (2013.01); *A61N 1/0468* (2013.01); *C08G 2101/00* (2013.01); *C08G 2101/0008* (2013.01)

(58) Field of Classification Search
CPC .... A61L 26/0019; A61L 15/26; A61L 15/425; A61L 26/0066; A61L 26/0085; A61L 2300/252; C08G 18/5072; C08G 18/834; C08G 18/837; C08G 18/3876; C08G 18/3893; A61F 13/00068; A61F 2013/00174; A61M 1/0088
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Kelling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery.
Susan Mendez-Eatmen, RN; "When Wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/the British Association of Plastic Surgeons, UK.

(Continued)

*Primary Examiner* — Sean Basquill
(74) *Attorney, Agent, or Firm* — Harness, Dickey & Pierce, P.L.C.

(57) ABSTRACT

The present disclosure provides sulfhydryl-modified polymer foams, which may be used for wound dressing materials. For example, the modified materials can include free sulfhydryl group, which can serve as a linker to attach biologically active molecules. For example, sulfhydryl groups can be used to conjugate biologically active polypeptides and/or metals to foam polymers. Methods for using sulfhydryl-modified polymers, such as for wound dressings, are also provided.

12 Claims, 6 Drawing Sheets

(56) References Cited

U.S. PATENT DOCUMENTS

| | | |
|---|---|---|
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,929,706 A * | 5/1990 | Heifetz ............... C12N 5/0037 528/49 |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0146382 A1 * | 10/2002 | Mallo ............... A61K 8/898 424/70.122 |
| 2005/0215701 A1 * | 9/2005 | Porsch ............... C08G 18/10 524/589 |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 0510393 * | 4/1992 | ............. B01J 20/32 |
| EP | 1018967 A1 | 7/2000 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/10424 A1 | 9/1990 | |
| WO | 93/09727 A1 | 5/1993 | |
| WO | 94/20041 A1 | 9/1994 | |
| WO | 96/05873 A1 | 2/1996 | |
| WO | 97/18007 A1 | 5/1997 | |
| WO | 99/13793 A1 | 3/1999 | |

OTHER PUBLICATIONS

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

(56) References Cited

OTHER PUBLICATIONS

Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, the Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," In II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

\* cited by examiner

SULFHYDRYL-FUNCTIONALIZED POLYMERIC COMPOSITIONS FOR MEDICAL DEVICES

CROSS-REFERENCE TO RELATED APPLICATION

This application claims priority to U.S. Provisional Application No. 61/718,130, filed Oct. 24, 2012, the disclosure of which is hereby incorporated by reference in its entirety.

FIELD

The present disclosure relates generally to functionalized polymeric material compositions, healing of wounds and wound-treatment therapies. More particularly, but not by way of limitation, the present disclosure relates to modified materials, for example, sulfhydryl-modified polyurethane foams for use in binding metals and biologically active components.

BACKGROUND INFORMATION

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. One of the major clinical benefits of negative pressure wound therapy is its ability to effectively eliminate wound exudate, thereby reducing edema and allowing tissue decompression. However, in these processes the polymer foams used for application of negative pressure therapy are typically biologically inert. In certain, aspects it may be beneficial provide active foams that provide additional therapy at a wound site. For example, improved materials with the ability to delivery and/or capture biologically active components would be desirable.

SUMMARY

The present disclosure provides novel polymeric materials, such as polymeric foams including sulfhydryl-modified polymers, which may be used to construct medical devices, or as wound dressing materials. Such modified polymers can, in some aspects, be used to bind biologically active components or agents, such as metals and/or polypeptides to the device.

Described herein are functionalized materials comprising sulfhydryl-functionalized polymer. Described herein are also functionalized foams, such as sulfhydryl-functionalized polymer foam. The foam may contain one or more copolymers. Polymers that may be functionalized with an sulfhydryl group include but are not limited to hydrophobic or hydrophilic polyurethanes, crosslinked and/or uncrosslinked polyolefins, polyols, ethylene vinyl acetate (EVA), elastomers such as acrylonitrile butadiene (NBR), polychloroprene (PCP or CR), ethylene propylene rubber (EPR & EPDM), poloxamers, silicones, polyvinyl alcohol, polypropylene, polystyrene, poloxamer, polyester, or fluoro carbon polymers or a combination thereof. The polymer may be polyurethane. The functionalized foam may be a polyurethane-based foam.

In some embodiments, the sulfhydryl-functionalized polymer foam may comprise a polymer, such as polyurethane, copolymerized with a sulfhydryl containing molecule, having the structure of formula (I). In other embodiments, the polymer foam provided herein relates to a polyurethane-based polymer copolymerized with a sulfhydryl siloxane having the formula according to:

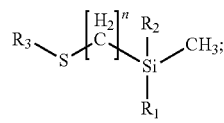

(I)

wherein
one of $R_1$ and $R_2$ forms a first covalent bond with the polymer, such as the polyurethane-based polymer foam, and the other is OH, $OCH_3$, $O(CH2)_{1-4}CH_3$, or a second covalent bond with the polymer;
n is 1-30; and
$R_3$ is H, or a covalent bond, for example with an adapter, a crosslinker, or a biologically active component or agent.
In some such embodiments, the covalent bond formed between $R_1$ or $R_2$ and the polymer is through an ester or a carbamate linkage. In other embodiments, the covalent bond formed between $R_3$ and the biologically active component or agent may be a disulfide or thioether linkage.

Examples of other molecules containing a sulfhydryl group that may be copolymerized with a polymer include but are not limited to bifunctional branched or non-branched hydroxyl-PEG-thiol compounds ranging from 1 kDa to 60 kDa, bifunctional branched or non-branched amine-PEG-thiol compounds ranging from 1 kDa to 60 kDa, bifunctional branched or non-branched HOOC-PEG-thiol compounds ranging from 1 kDa to 60 kDa, bifunctional branched or non-branched hydroxyl-polyol-thiol compounds ranging from 1 kDa to 60 kDa, bifunctional branched or non-branched amine-polyol-thiol compounds ranging from 1 kDa to 60 kDa, bifunctional branched or non-branched HOOC-polyol-thiol compounds ranging from 1 kDa to 60 kDa, 2-(Triethoxysilylpropoxy) ethoxysulfolane, Trimethylsilylmethyltrifluoromethane sulfonate, Trimethylsilylpropanesulfonic acid, Trimethylsilylmethanesulfonate, Trimethylsilyl isocyanate, N-(Trimethoxysilylpropyl) isothioronium chloride, 2-(3-Trimethoxysilylpropylthio) thiophene, 2-(Trimethylsilyl) phenyltrifluoromethanesulfonate, Trimethylsilylchlorosulfonate, 3-(Trihydroxysilyl)-1-Propanesulfonic acid, Trimethylsilylperfluoro-1-butanesulfonate, Trimethylsilyltrifluoromethanesulfonate, O-(2-Carboxyethyl)-O'-(2-mercaptoethyl)heptaethylene glycol, D-penicillamine, glutathione, or Cleland's reagent.

In additional embodiments, the copolymeric material or foam described above further comprises a plurality of covalently attached adapters, such as the adapter of formula (I). In some embodiments, the adapter or copolymer molecules react with one another forming Si—O—Si dimers, trimers, or long chains that may be incorporated as large block molecules into the foam or as large monolayers onto the foam. Furthermore in some embodiments, the covalently attached copolymer is present in a ratio of from about 1 to about 40 parts per hundred of the polymer. The covalently attached adapter may also be present in a ratio of about 1-2 adapter(s) per polyol/copolymer molecule.

The polymer foams described herein may have a variety of structures. For example, FIG. 1 depicts an exemplary foam in which the foam backbone comprises pegylated polyols copolymerized with silane sulfhydryl copolymers.

Described herein are a functionalized material and foam comprising a polymer copolymerized with a sulfhydryl-polyol or sulfhydryl-polyethylene glycol (PEG) (also known as PEG-sulfhydryl). The functionalized material or foam may be covalently attached with an adapter and/or a crosslinker. The functionalized material or foam may also be covalently attached with a crosslinker through an adapter on the foam or material. A biologically active component or agent may be attached to the functionalized material or foam through the crosslinker.

Described herein are also polymer foams, such as polyurethane-based polymer foams, further comprising a covalently attached adapter and crosslinker. In one embodiment, the crosslinker is attached to the foam through the adapter, and the adapter is attached directly to the foam. In other embodiments, the crosslinker is directly attached to copolymers in the foam. In some cases, the adapter and co-polymer begin as the same molecule type, but evolve different bond configurations depending on how they are attached or co-polymerized into the structure.

In some embodiments, the foam described herein further comprises a biologically active component or agent. The foam may be a copolymer foam comprising one or more polymers and a sulfhydryl containing molecule. The copolymer foam may be a polyurethane-based foam, and the sulfhydryl containing molecule may be the sulfhydryl siloxane of formula (I). In one embodiment, the biologically active component may be attached directly to the copolymer. In another embodiment, the copolymer foam may comprise an adapter, such as a sulfhydryl containing molecule, for example the molecule of formula (I), and the biologically active component or agent may be attached to the copolymer foam through the adapter.

The foam may be a polyurethane-based foam and may further comprise an adapter and a crosslinker for covalently attaching the biologically active component or agent. In one embodiment, the biologically active component or agent is covalently attached to the crosslinker, and the crosslinker is covalently attached to the polyurethane-based foam through the adapter, which is covalently attached to the foam. The adapter may be a sulfhydryl containing molecule.

Biologically active components or agents may be therapeutic agents, such as polypeptides and metals. As an example, the therapeutic agents may be linked to the foam via a disulfide bridge to the copolymerized silane sulfhydryl. FIG. 2 depicts an exemplary foam in which the foam backbone comprises polymerized pegylated polyols. In such embodiments, silane sulfhydryl moieties can be used as adapters, by silanating a hydroxyl group of the polyurethane foam. In such foams, polypeptides, metals, or other therapeutic agents may be linked to the foam via a disulfide bridge to the silane sulfhydryl adapter. In a combination of the exemplary foams of FIGS. 1 and 2, FIG. 3 depicts an exemplary foam in which the foam backbone comprises pegylated polyols copolymerized with silane sulfhydryl copolymers and which further comprises silane sulfhydryl moieties that can be used as adapters. Polypeptides, metals, and other therapeutic agents may be linked to the foam via a disulfide bridge to the copolymerized silane sulfhydryl and also may be linked to the foam via a disulfide bridge to the silane sulfhydryl adapters.

In some embodiments, $R_3$ is a covalently attached therapeutic agent. For example, the therapeutic agent may be, but is not limited to, any of the following: peptides, polypeptides, enzymes, peptide, protein, and enzyme matrices, antibodies, ligands, carbohydrates, lipids, oligonucleotides, antimicrobials, small molecules, nanoparticles, nanobots, aliphatic hydrocarbon chains, surfactants, metals, alginates, aptamers, dendrimers, arborols, or a combination thereof. The wound dressing may be a multifunctional dressing comprising one or more biologically active components or agents. The therapeutic agent may be covalently attached to the modified polymer via a chemical linkage. Also, in some embodiments, $R_3$ can be a metal cation in the +1, or +2 state, and present in either a salt or elemental form. Exemplary, non-limiting embodiments of such metal cations include: copper, zinc, sodium, lithium, potassium, calcium, magnesium, iron, cadmium, gold, and silver.

Described herein are wound dressings comprising the polymer foams described above. The wound dressing may comprise a polymer foam and a biologically active component or agent. The wound dressing may further comprise a drape covering the polymer foam.

The polymer foams and wound dressings described herein may be adapted to serve as an electrical conductor or to enhance the conductivity of a solution, during use.

In some embodiments, the polymer foam is a reticulated open-celled foam. The polymer foam may be a polyurethane-based foam. The polyurethane-based polymer foam may comprise, in addition to the sulfhydryl containing molecule, an additional copolymer such as but not limited to polyvinyl alcohol, polypropylene, polystyrene, polyols, poloxamer, or a combination of one or more of these.

Provided herein are methods for treating wounds comprising contacting a wound site with a wound dressing as discussed above. In some embodiments, these methods also can involve negative pressure wound therapy provision in conjunction with the use of the dressing. The method may also involve applying an instillation solution with negative pressure wound therapy.

Some specific embodiments may comprise methods of providing an electrical current to a wound site comprising: (a) contacting the wound site with a wound dressing as described above; (b) applying an electrical current to the wound dressing, a wound bed, or a periwound area; or (c) applying the current to a fluid in contact with the wound dressing, or wound.

The methods provided herein also relate to methods of producing the polymeric material or foam described above comprising copolymerizing a diisocyanate and a polyol in the presence of a molecule containing a sulfhydryl group. In some specific embodiments, the molecule is an alkoxysilane molecule, such as (3-Mercaptopropyl) methyldimethoxysilane. In other specific embodiments, the sulfhydryl-containing molecule is D-penicillamine, glutathione, or Cleland's reagent.

Described herein are methods of producing polymeric material or foams comprising copolymerizing a diisocyanate and a polyol to form a polymer foam, covalently attaching an adapter to the foam, and covalently attaching a crosslinker to the foam through the adapter.

The materials described herein comprise a polyurethane-based material, sheet, solid or semi-solid membrane, permeable or semi-permeable membrane, interfacial layer. The polyurethane-based material may also be used as a coating for beads, catheter, stent, or other devices.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE EMBODIMENTS

In some aspects, the present disclosure provides sulfhydryl-modified materials, such as foams, which may be used, in some embodiments, as wound inserts or dressings. Such modified materials can be used for catching and concentrating specific factors in the wound environment, for example, factors triggering a biological response such as angiogenesis, or to deliver biomolecules or bioactive compounds to a wound bed. Likewise, such materials may be coupled to biologically active components such as recombinant polypeptides to enhance wound therapy. In still further aspects, the materials can be coupled to metals thereby allowing the foams to conduct an electrical current. Thus, in some embodiments, the biologically active components or agents are endogenous, while in others they are exogenous.

In one aspect, modified foams are produced by copolymerizing a sulfhydryl containing molecule with a polymer to form a polymer foam, such as a polyurethane foam. The molecule is copolymerized in a way that leaves the sulfhydryl group available for chemical reactions. For example, an organosilane comprising a sulfhydryl group (e.g., (3-Mercaptopropyl) methyldimethoxysilane) can be employed. Thus, in some aspects a copolymer has a general structure of:

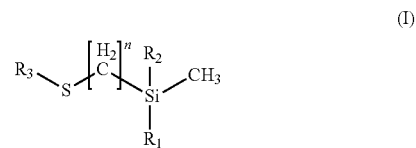

(I)

where at least one of $R_1$ and $R_2$ is an ester or carbamate linkage to the polyurethane-based polymer foam. In this formula $R_3$ is a linkage to a molecule comprising a biologically active component or agent, such as a polypeptide (e.g., attached via a disulfide linkage) or an ionically or electrostatically bound metal. Other examples of sulfhydryl containing molecules include but are not limited to D-penicillamine, glutathione, or Cleland's reagent.

Figure 1:
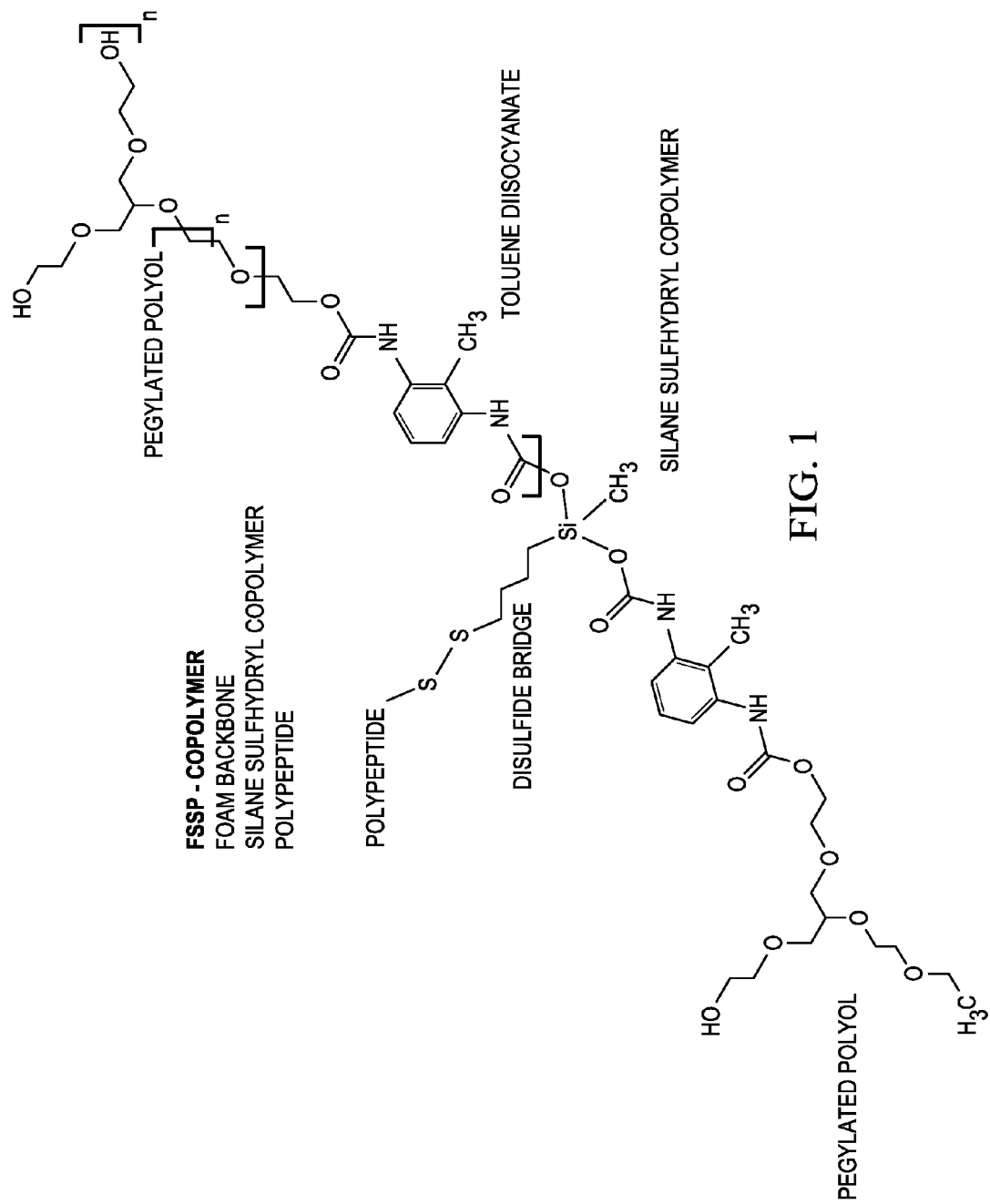
FIG. 1 depicts an exemplary foam in which the foam backbone comprises pegylated polyols copolymerized with silane sulfhydryl copolymers. Polypeptides and metals may be linked to the foam via a disulfide bridge to the copolymerized silane sulfhydryl.
Figure 2:
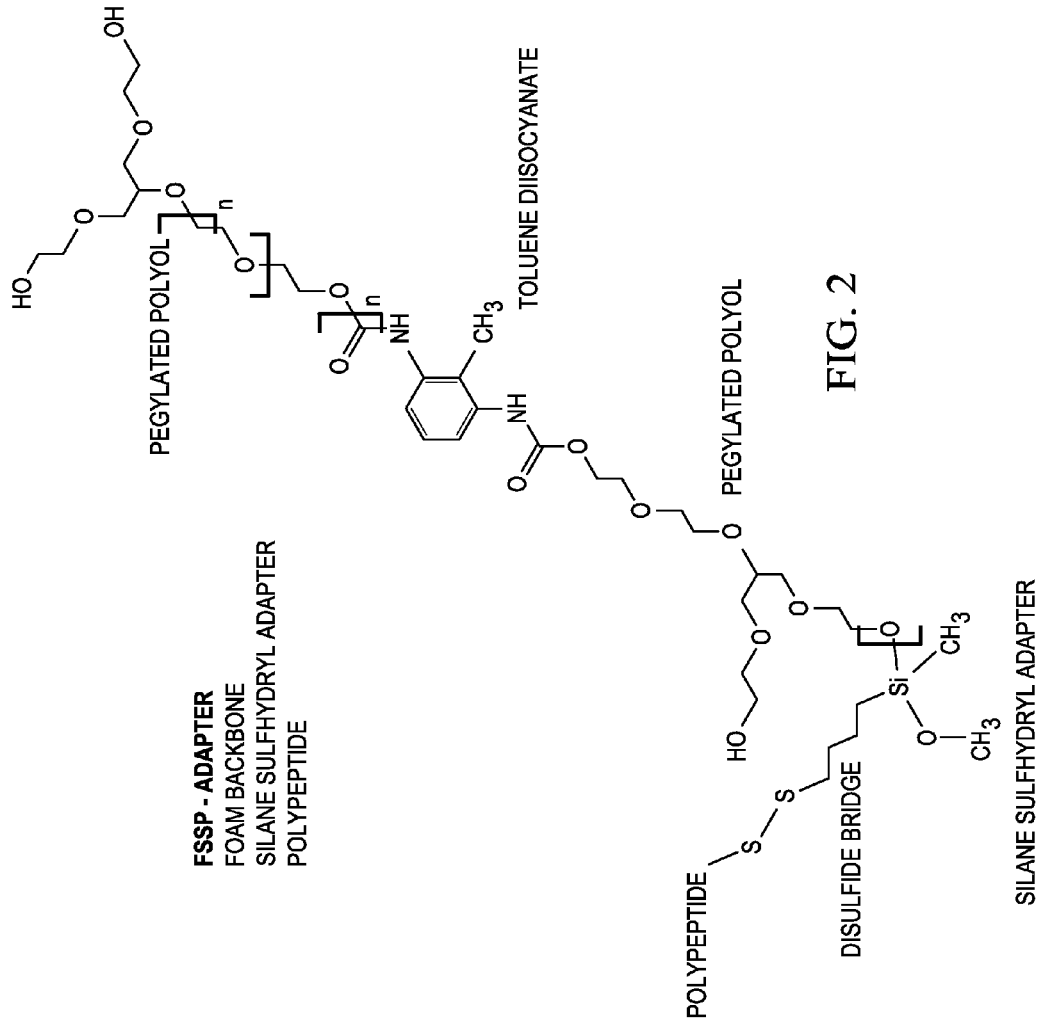
FIG. 2 depicts an exemplary foam in which the foam backbone comprises polymerized pegylated polyols. In such embodiments, silane sulfhydryl moieties can be used as adapters, by silanating a hydroxyl group of the polyurethane foam. In such foams, polypeptides and metals may be linked to the foam via a disulfide bridge to the silane sulfhydryl adapter.
Figure 3:
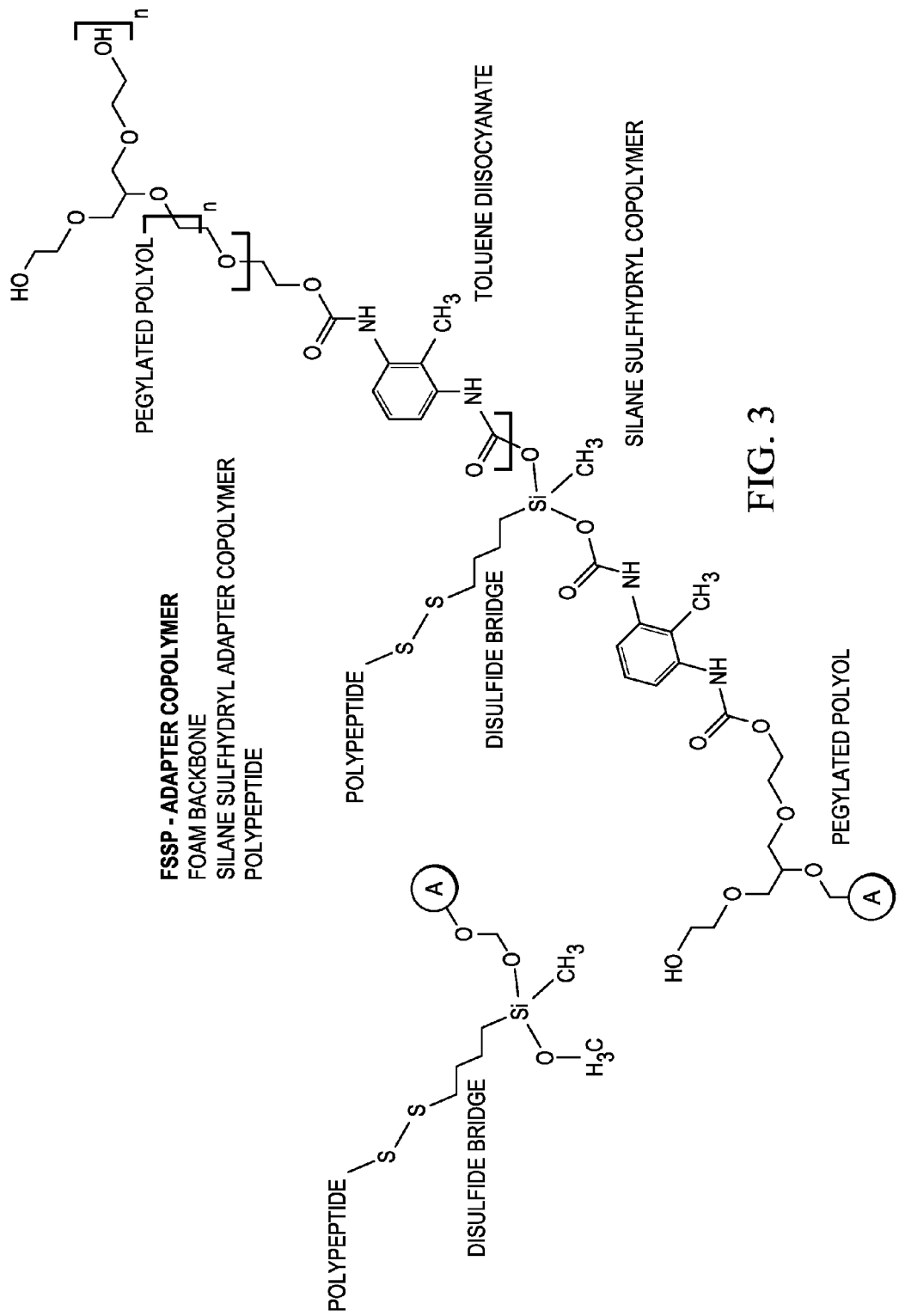
FIG. 3 depicts an exemplary foam in which the foam backbone comprises pegylated polyols copolymerized with silane sulfhydryl copolymers and which further comprises silane sulfhydryl moieties that can be used as adapters. Polypeptides and metals may be linked to the foam via a disulfide bridge to the copolymerized silane sulfhydryl and also may be linked to the foam via a disulfide bridge to the silane sulfhydryl adapters.

Such copolymers provide covalently integrated sulfhydryl groups into the foam, which can be engineered with disulfide bridges and other linkages for biomolecules (FIG. 1). This means that reactive sulfhydryl groups—e.g., from a cysteine residue, a thiol-engineered molecule, or other—can be used to covalently attach/detach molecules to the sulfhydryl groups polymerized in the foam. In some aspects, the attachment/detachment can be performed with a simple adjustment to pH by an acid or base, or the introduction of an oxidizing agent. Thus, any molecule with a free, reactive, sulfhydryl can be induced to attach/detach, to/from the foam with this chemistry. In the case of the reversible S—S bond, this allows for potential biodegradation of the covalently attached ligand (and thereby releases components at the wound site). Using disulfide bridges to bind biomolecules to the foam can also abrogate the need for crosslinkers or adapters, avoiding potential toxicity and compatibility issues that may occur with crosslinkers.

In further aspects, reactive sulfhydryls can be used to produce metallic foams. In this case the thiol groups are used for ionic linkage of metals, including heavy metals, such as gold silver, and copper. When sufficient amounts of the metals are bound to the foam, the foam can be used as a circuit to channel electricity. Thus, this platform can be used as a means to produce an electrical stimulation dressing. Furthermore, in some aspects, the wound dressing can be configured as a voltaic cell to produce its own current. In this instance, one end of the dressing (cathode) could contain positively charged metals and the other end can contain negatively charged (anode) components. In a wound environment, this would produce and conduct a microcurrent. Such microcurrents have been shown to improve epithelialization, and thereby provide methods for enhanced wound healing.

Binding heavy metals also has potential benefits in fighting or killing microbes. In particular, certain metals (such as silver) disrupt microbial membranes and impair the oxidative respiration of microorganisms. With reactive sulfhydryls polymerized in the foam, metals in the +1 or +2 cationic state can be ionically bound to the wound insert. Thus, metals such copper can be bound to the foam.

In further aspects, bonding of metals to the sulfhydryl groups can be used for sequestering harmful proteases. For example, positively charged zinc and calcium ions catalyze the activity of harmful proteases, such as MMPs. These metals catalyze this activity by binding to protease cofactor sites, away from the active site, in an orientation that exposes the active site and enables the proteolytic function of the MMP. Thus, sulfhydryl groups of the foams can be used to sequester such metals and/or be bound to metals to catch and/or sequester MMPs by their cofactor binding site (zinc and calcium).

The sulfhydryl-modified foams of the embodiments therefore provide platforms for capture of biomolecules; drug/antimicrobial/nanoparticle delivery; detection/diagnostics (e.g., of bound components); bioelectric devices; regulation of the wound environment; electrical current wound stimulation; and/or biodegradation/reabsorption of bound ligands.

A. DEFINITIONS

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "thioether" means —S—; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); and "sulfinyl" means —S(O)— (see below for definitions of groups containing the term sulfinyl, e.g., alkylsulfinyl).

The symbol "—" means a single bond, "=" means a double bond, and "≡" means triple bond. The symbol "----" represents an optional bond, which if present is either single or double. The symbol "====" represents a single bond or a double bond. Thus, for example, the structure

includes the structures

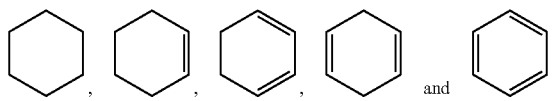

As will be understood by a person of skill in the art, no one such ring atom forms part of more than one double bond. The symbol "〰", when drawn perpendicularly across a bond indicates a point of attachment of the group. It is noted that the point of attachment is typically only identified in this manner for larger groups in order to assist the reader in rapidly and unambiguously identifying a point of attachment. The symbol "◤■" means a single bond where the group attached to the thick end of the wedge is "out of the page." The symbol "⦀" means a single bond where the group attached to the thick end of the wedge is "into the page". The symbol "〰" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

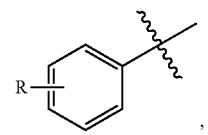

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

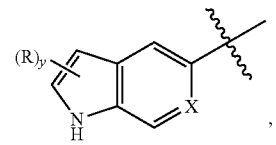

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group.

Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neopentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

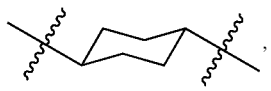 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

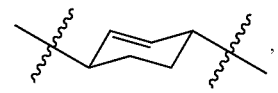 [SMILES: *C1C=CC(*)CC1]

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups, —CH=CHF, —CH=CHCl and —CH=CHBr, are non-limiting examples of substituted alkenyl groups. An "alkene" refers to the compound H—R, wherein R is alkenyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

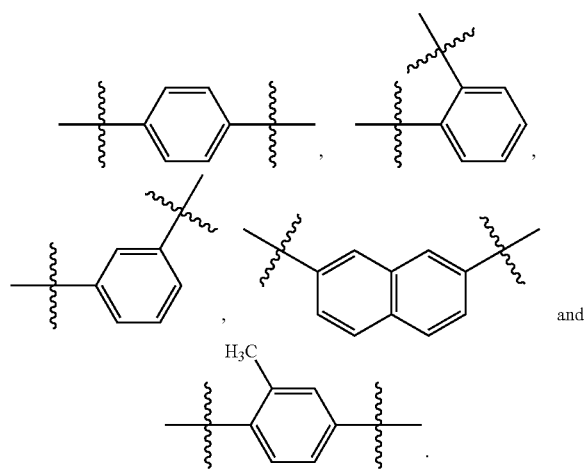

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. Non-limiting examples of substituted aralkyls are: (3-chlorophenyl)-methyl, and 2-chloro-2-phenylethlyl.

The term "heteroaryl" when used without the "substituted" modifier refers to a monovalent aromatic group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the group consists of no atoms other than carbon, hydrogen, aromatic nitrogen, aromatic oxygen and aromatic sulfur. As used herein, the term does not preclude the presence of one or more alkyl group (carbon number limitation permitting) attached to the aromatic ring or any additional aromatic ring present. Non-limiting examples of heteroaryl groups include furanyl, imidazolyl, indolyl, indazolyl (Im), methylpyridyl, oxazolyl, pyridyl, pyrrolyl, pyrimidyl, pyrazinyl, quinolyl, quinazolyl, quinoxalinyl, thienyl, and triazinyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of heteroarenediyl groups include:

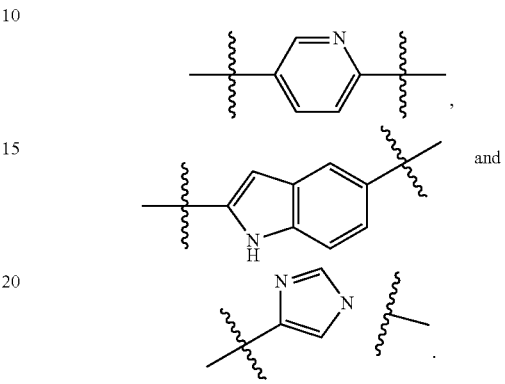

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O—cyclopentyl, and —O—cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. Similarly, the term "alkylthio" when used without the "substituted" modifier refers to the group —SR, in which R is an alkyl, as that term is defined above. The term "alkoxydiyl" when used without the "substituted" modifier refers to the divalent group —O-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "glycoside" refers to a compound in which a sugar group is bound to a non-carbohydrate moiety. Typically the sugar group (glycone) is bonded through its anomeric carbon to another group (aglycone) via a glycosidic bond that has an oxygen, nitrogen or sulfur atom as a linker.

A "simple sugar" is the basic structural units of carbohydrates, which cannot be readily hydrolyzed into simpler units. The elementary formula of a simple monosaccharide is $C_nH_{2n}O_n$, where the integer n is at least 3 and rarely greater than 7. Simple monosaccharides may be named generically according on the number of carbon atoms n: trioses, tetroses, pentoses, hexoses, etc. Simple sugars may be open chain (acyclic), cyclic or mixtures thereof. In these cyclic forms, the ring usually has 5 or 6 atoms. These forms are called furanoses and pyranoses, respectively—by analogy with furan and pyran. Simple sugars may be further classified into aldoses, those with a carbonyl group at the end of the chain in the acyclic form, and ketoses, those in which the carbonyl group is not at the end of the chain. Non-limiting examples of aldoses include: glycolaldehyde, glyceraldehydes, erythrose, threose, ribose, arabinose, xylose, lyxose, allose, altrose, glucose, mannose, gulose, idose, galactose and talose. Non-limiting examples of aldoses include: dihydroxyacetone, erythrulose, ribulose, xylulose, fructose, psicose, sorbose and tagatose. The 'D-' and 'L-' prefixes may be used to distinguish two particular stereoisomers which are mirror-images of each other. The term simple sugar also covers O-acetyl derivatives thereof.

An "amino sugar" or "aminoglycoside" refers to a derivative of a sugar, deoxy sugar, sugar acid or sugar alcohol, where one or more hydroxy group(s) has been replace with one more amino group(s). An "amino sugar" refers to a derivative of a simple sugar, simply deoxy sugar, simply sugar acid or sugar alcohol, where one or more hydroxy group(s) has been replace with one more amino group(s). These terms also cover N- and O-acetyl derivatives thereof. Non-limiting examples include N-acetylglucosamine, galactosamine, glucosamine and sialic acid.

The term "deoxy sugar" refers to a sugar derivative where one of the hydroxy groups of a carbohydrate has been replaced with a hydrogen atom. A "simple deoxy sugar" is a deoxy sugar derived from a simple sugar, as defined herein. These terms also cover O-acetyl derivatives thereof. Non-limiting examples of simple deoxy sugars are deoxyribose (based upon ribose), fucose, and rhamnose.

The term "sugar acid" refers to a sugar derivative where an aldehyde functional group or one or more hydroxy functional groups has been oxidized to a carboxyl group. Aldonic acids are those in which the aldehyde functional group of an aldose has been oxidized. Ulosonic acids are those in which the first hydroxyl group of a 2-ketose has been oxidized creating an α-ketoacid. Uronic acids are those in which the terminal hydroxyl group of an aldose or ketose has been oxidized. Aldaric acids are those in which both ends of an aldose have been oxidized. Non-limiting aldonic acids include glyceric acid (3C), xylonic acid (5C), gluconic acid (6C), and ascorbic acid (6C, unsaturated lactone). Non-limiting examples of ulosonic acids include neuraminic acid (5-amino-3,5-dideoxy-D-glycero-D-galacto-non-2-ulosonic acid) and ketodeoxyoctulosonic acid (KDO or 3-deoxy-D-manno-oct-2-ulosonic acid). Non-limiting examples of uronic acids include glucuronic acid (6C), galacturonic acid (6C), and iduronic acid (6C). Non-limiting example of aldaric acids include tartaric acid (4C), meso-galactaric acid (mucic acid) (6C), and D-glucaric acid (saccharic acid) (6C). A "simple sugar acid" is a sugar acid derived from a simple sugar. These terms also cover O-acetyl derivatives thereof.

The term "sugar alcohol" refers to a sugar derivative whose carbonyl group (aldehyde or ketone, reducing sugar) has been reduced to a primary or secondary hydroxyl group. Non-limiting examples of sugar alcohols include: glycol (2-carbon), glycerol (3-carbon), erythritol (4-carbon), threitol (4-carbon), arabitol (5-carbon), xylitol (5-carbon), ribitol (5-carbon), mannitol (6-carbon), sorbitol (6-carbon), dulcitol (6-carbon), iditol (6-carbon), isomalt (12-carbon), maltitol (12-carbon), lactitol (12-carbon) or polyglycitol. A "simple sugar alcohol" is a sugar alcohol derived from a simple sugar. These terms also cover O-acetyl derivatives thereof.

As used herein, the term "monosaccharide group" refers to a monovalent carbohydrate group, with a carbon atom as the point of attachment. The term covers the groups resulting from removal of a hydroxyl radical from a simple sugar (e.g., glucose), simple deoxy sugar (e.g., fucose), simple sugar acid (e.g., gluconic acid), simple sugar alcohol (e.g., xylitol) or simple amino sugar (e.g., glucosamine). Typically the monosaccharide group is bonded through its anomeric carbon to another group (aglycone) via oxygen atom linker. In some cases the linker may be a nitrogen or sulfur atom.

A "disaccharide group" is a monovalent carbohydrate group consisting of two monosaccharide groups, wherein the second monosaccharide group replaces a hydrogen on a hydroxy group of the first monosaccharide group. Non-limiting examples of disaccharide groups include those derived from sucrose, lactulose, lactose, maltose trehalose and cellobiose.

A "trisaccharide group" is a monovalent carbohydrate group consisting of three monosaccharide groups, wherein the second monosaccharide group replaces a hydrogen on a hydroxy group of the first monosaccharide group and the third monosaccharide group replaces a hydrogen on a hydroxy group of either the first or the second monosaccharide groups.

An oligosaccharide is a monovalent carbohydrate group consisting of three to ten, preferably three to six monosaccharide groups, wherein the second monosaccharide replaces a hydrogen on a hydroxy group of the first monosaccharide, the third monosaccharide replaces a hydrogen on a hydroxy group of either the first or the second monosaccharide groups, and subsequent monosaccharide groups replace hydrogens on any previously joined monosaccharide groups, thus forming either a linear or branched structure.

The term "silyl" when used without the "substituted" modifier refers to the group —SiR$_3$, where each R is independently hydrogen or unsubstituted alkyl, as that group is defined above. The term "substituted silyl" refers to the group, —SiR$_3$, wherein at least one of the R groups and as many as all of the R groups, is independently a substituted alkyl or —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. Any remaining R groups of the substituted silyl group are independently hydrogen or unsubstituted alkyl. The term "silylated" or "silanated" indicates that a given compound has been derivatized to contain a silyl and/or substituted silyl group. The abbreviation "-Sil" refers to silyl and/or substituted silyl groups.

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a wound dressing that "comprises," "has," "includes" or "contains" one or more elements possesses those one or more elements, but is not limited to possessing only those elements. For example, in a wound dressing that comprises a wound insert and a drape, the wound dressing includes the specified elements but is not limited to having only those elements. For example, such a wound dressing could also include a connection pad configured to be coupled to a wound-treatment apparatus.

The term "effective," as that term is used in the specification and/or claims, means adequate to accomplish a desired, expected, or intended result.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"PBS" is phosphate buffered saline; "phr" is parts per hundred resin; "OPA" is ortho-pthaldialdehyde; "RT" is room temperature.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo [2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt described herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "polymer" includes "copolymers."

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[CH$_2$CH$_2$]$_n$—, the repeat unit is —CH$_2$CH$_2$—. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc.

The term "reticulated open cell foam" or ROCF refers to a foam material with a porous structure consisting of an interconnected network of solid struts. The open cells are formed by the reticulation process, which is in turn defined as in the form of a network or having a network of parts. Because all struts are connected, the open cell porosity is also connected creating a continuously porous material. The ROCF can be defined specifically by three independent properties; pore size, relative density, and base material. In some embodiments, ROCF is made from polyurethane.

The above definitions supersede any conflicting definition in any of the reference that is incorporated by reference herein. The fact that certain terms are defined, however, should not be considered as indicative that any term that is undefined is indefinite. Rather, all terms used are believed to describe the embodiments in terms such that one of ordinary skill can appreciate the scope and practice the embodiments.

Further, a device or structure that is configured in a certain way is configured in at least that way, but it can also be configured in other ways than those specifically described.

B. SULFHYDRYL-MODIFIED MATERIALS

In one aspect the present embodiments provide a covalent system for copolymerizing sulfhydryl containing molecules, or attaching a sulfhydryl groups to polyurethane foams. Such that in some aspects, the sulfhydryl groups can in turn be used to bind biologically active components. In some case, these components can be used for catching and concentrating specific factors in the wound environment, including factors that trigger a significant biological response, such as proliferation, differentiation, or angiogenesis. This technology may be used, for example, to deliver biomolecules or bioactive compounds to the wound bed. Sulfhydryl-modified materials provided herein may be used in some embodiments as a system for catching and concentrating specific factors in the wound environment, for example, factors triggering a biological response such as angiogenesis, or to deliver endogenous or exogenous biomolecules or bioactive compounds to the wound bed.

In one aspect, the sulfhydryl-modified materials, such as polymer foams, comprise a copolymer having one or more polymers, such as polyurethane, copolymerized with a sulfhydryl containing molecule. In some aspects, sulfhydryl-modified materials further comprise a biologically active component or agent attached via the sulfhydryl group incorporated into the foam. The polymer foam may further comprise a covalently attached adapter. The adapter may be the sulfhydryl siloxane of formula (I). In other aspects, a biologically active molecule can be directly attached to a functional group of the polymer foam. The biologically active molecule also can be attached to the foam by way of the adapter that is covalently attached to the foam.

In another aspect, the sulfhydryl-modified materials, such as polymer foams, comprise one or more polymers, such as polyurethane, covalently attached with an adapter. The adapter may be the sulfhydryl siloxane of formula (I). The polymer foam may further comprise a crosslinker covalently attached to the adapter. A biologically active molecule may be covalently attached to the polymer foam through the crosslinker and the adapter attached to the foam.

The biologically active molecule may be covalently attached to the foam using other known physical and/or chemical methods, including but not limited to methods involving temperature, pressure, pH, radiation, light, UV light, freeze-drying, and/or sterilization.

The adapters and crosslinkers for attaching the biologically active molecules may be reversible or cleavable. The adapters or crosslinkers may be cleaved by employing a solution, for example a solution having a specific pH.

A list of such exemplary crosslinkers are provided below in Table 1.

TABLE 1

Table shows potential crosslinker chemistries that could be used to link biologically active moieties to the sulfhydryl-modified foams of the embodiments (either directly or through a further chemical linkage). Several of these crosslinkers are cleavable or reversible, and thus they may be used as a vehicle for delivery of molecules into the wound environment if they are coupled with an appropriate solution.

Homobifunctional Crosslinkers. A list of crosslinking reagents that have the same type of reactive group at either end. Reagents are classified by what chemical groups they crosslink (left column) and their chemical composition (middle column). Products are listed in order of increasing length within each table cell.

| Crosslinking Target | Crosslinker Reactive Groups, Features | Crosslinker Products |
|---|---|---|
| Sulfhydryl-to-Sulfhydryl | Maleimides | BMOE |
| | | BMB |
| | | BMH |
| | | TMEA (trifunctional) |
| | Maleimides, PEG spacer | BM(PEG)2 |
| | | BM(PEG)3 |
| | Maleimides, cleavable | BMDB |
| | | DTME |

Heterobifunctional Crosslinkers. A list of crosslinking reagents that have the different reactive groups at either end. Reagents are classified by what chemical groups they crosslink (left column) and their chemical composition (middle column). Products are listed in order of increasing length within each table cell.

| Crosslinking Target | Crosslinker Reactive Groups, Features | Crosslinker Products |
|---|---|---|
| Amine-to-Sulfhydryl | NHS ester/Maleimide | AMAS |
| | | BMPS |
| | | GMBS and |
| | | Sulfo-GMBS |
| | | MBS and |

TABLE 1-continued

Table shows potential crosslinker chemistries that could be used to link biologically active moieties to the sulfhydryl-modified foams of the embodiments (either directly or through a further chemical linkage). Several of these crosslinkers are cleavable or reversible, and thus they may be used as a vehicle for delivery of molecules into the wound environment if they are coupled with an appropriate solution.

|  |  |  |
|---|---|---|
|  |  | Sulfo-MBS |
|  |  | SMCC and |
|  |  | Sulfo-SMCC |
|  |  | EMCS and |
|  |  | Sulfo-EMCS |
|  |  | SMPB and |
|  |  | Sulfo-SMPB |
|  |  | SMPH |
|  |  | LC-SMCC |
|  |  | Sulfo-KMUS |
|  | NHS ester/Maleimide, | SM(PEG)2 |
|  | PEG spacer | SM(PEG)4 |
|  |  | SM(PEG)6 |
|  |  | SM(PEG)8 |
|  |  | SM(PEG)12 |
|  |  | SM(PEG)24 |
|  | NHS ester/Pyridyldithiol, | SPDP |
|  | cleavable | LC-SPDP |
|  |  | and |
|  |  | Sulfo-LC-SPDP |
|  |  | SMPT |
|  |  | Sulfo-LC-SMPT |
|  |  | PEG4-SPDP |
|  |  | PEG12-SPDP |
|  | NHS esters/Haloacetyl | SIA |
|  |  | SBAP |
|  |  | SIAB |
|  |  | Sulfo-SIAB |
| Sulfhydryl-to-Carbohydrate | Maleimide/Hydrazide | BMPH |
|  |  | EMCH |
|  |  | MPBH |
|  |  | KMUH |
|  | Pyridyldithiol/Hydrazide | PDPH |
| Hydroxyl-to-Sulfhydryl | Isocyanate/Maleimide | PMPI |

Examples of other crosslinkers for linking a biologically active component or agent to the polymer foam include but are not limited to malondialdehyde, succinaldehyde, pthaldehyde, glutaraldehyde, or glyoxal.

In other embodiments, the biologically active molecule, such as a therapeutic agent, may be covalently attached to the polyurethane-based foam through a crosslinker, covalently attached to an adapter, which is conjugated to the foam. The polyurethane-based foam may not include a sulfhydryl containing molecule. The adapter may be a sulfhydryl containing molecule.

1. Suitable Polymers

Polymers for use with the present embodiments include hydrophobic or hydrophilic polyurethanes, crosslinked and/or uncrosslinked polyolefins, polyols, ethylene vinyl acetate (EVA), elastomers such as acrylonitrile butadiene (NBR), polychloroprene (PCP or CR), ethylene propylene rubber (EPR & EPDM), poloxamers, silicones, polyvinyl alcohol, polypropylene, polystyrene, poloxamer, polyester, fluoro carbon polymers, or a combination thereof.

The foams described herein may comprise one or more polymers. For example, in some embodiments, the polymer may be a polyurethane polymer. In other embodiments, the polymer may be a blend of a polyurethane and one or more other copolymers, such as polyvinyl alcohol or polypropylene.

Polyurethanes are reaction polymers. A urethane linkage is produced by reacting an isocyanate group, $-N=C=O$ with a hydroxy group, and polyurethanes are produced by the polyaddition reaction of a polyisocyanate with a diol or a polyol, typically in the presence of a catalyst and other additives. A polyisocyanate is a molecule with two or more isocyanate functional groups, $R-(N=C=O)_n$, wherein $n \geq 2$ and a polyol is a molecule with two or more hydroxyl functional groups, $R'-(OH)_n$, wherein $\geq 2$. The reaction product is a polymer containing the urethane linkage, $-RNHCOOR'-$. Polyurethanes may be produced by reacting a liquid isocyanate with a liquid blend of water, polyols, surfactants, catalysts, and other additives. The blend of polyols and other additives may also be called a resin or a resin blend. In some aspects, the copolymer moiety acts in the polymerization reaction as a polyol and is therefore substituted for all or a portion of the polyol used in a polymerization reaction. In some embodiments, resin blend additives may include chain extenders, crosslinkers, surfactants, flame retardants, blowing agents, pigments, and/or fillers. The synthesis of breathable or air-permeable, open cell, flexible urethane polymers is taught for example by U.S. Pat. No. 5,686,501, which is incorporated by reference herein in its entirety.

Molecules that contain two isocyanate groups are called diisocyanates. Isocyanates may be classed as aromatic, such as diphenylmethane diisocyanate (MDI), diphenylethane diisocyanate (EDI), or toluene diisocyanate (TDI); or aliphatic, such as hexamethylene diisocyanate (HDI) or isophorone diisocyanate (IPDI). An example of a polymeric isocyanate is polymeric diphenylmethane diisocyanate, which is a blend of molecules with two-, three-, and four- or more isocyanate groups. Isocyanates can be further modified by partially reacting them with a polyol to form a prepolymer. A "quasi-prepolymer" is formed when the stoichiometric ratio of isocyanate to hydroxyl groups is greater than 2:1. A "true prepolymer" is formed when the stoichiometric ratio is equal to 2:1. Important characteristics of isocyanates include their molecular backbone, % NCO content, functionality, and viscosity.

Molecules that contain two hydroxyl groups are called diols. Examples include, ethylene glycol (EG), 1,4-butanediol (BDO), diethylene glycol (DEG). Molecules that contain three hydroxyl groups are called triols. Examples include glycerol. Polyols may themselves be polymers. For example, they may be formed by base-catalyzed addition of propylene oxide (PO), ethylene oxide (EO) onto a hydroxy or amino-containing initiator, or by polyesterification of a di-acid, such as adipic acid, with glycols, such as ethylene glycol or dipropylene glycol (DPG). Polyols extended with PO or EO are typically called polyether polyols. Polyols formed by polyesterification are typically called polyester polyols. The choice of initiator, extender, and molecular weight of the polyol will typically affect its physical state, and the physical properties of the resulting polyurethane. Important characteristics of polyols are their molecular backbone, initiator, molecular weight, % primary hydroxyl groups, functionality, and viscosity.

One attribute of polyurethanes is its ability to be turned into foam. As the reagents react with one another, carbon dioxide gas is created, which fills and expands cells created during the mixing process. Blowing agents may also be used, including certain halocarbons such as HFC-245fa (1,1,1,3,3-pentafluoropropane) and HFC-134a (1,1,1,2-tetrafluoroethane), and hydrocarbons such as n-pentane. In some embodiments, surfactants may be used to modify the characteristics of the polymer during the foaming process.

Though the properties of the polyurethane are typically determined mainly by the choice of polyol, the diisocyanate exerts some influence. For example, the cure rate will generally be influenced by the reactivity of a given functional group and the number of functional isocyanate groups.

Softer, elastic, and more flexible polyurethanes typically result when linear difunctional polyethylene glycol segments, commonly called polyether polyols, are used to create the urethane links. More rigid products typically result if polyfunctional polyols are used, as these create a three-dimensional cross-linked structure which, again, can be in the form of a low-density foam. Control of viscoelastic properties, for example, by modifying the catalysts and polyols used can lead to memory foam, which is much softer at skin temperature than at room temperature.

In some embodiments, the polyurethane foam is formed by the polymerization of isocyanates and polyols, typically toluene diisocyanate and a multi arm polyether polyol. These components may be indexed, such that the isocyanate and hydroxyl group are in a one to one ratio.

Formulations of various PHR (grams of [component] Per Hundred grams of polyurethane Resin) of sulfhydryl molecules, have been produced and tested. They have been characterized by the amount of surface sulfhydryl available for bonding by conjugation of the foam with a dye. The relative fluorescence units RFU were found to be proportional to the amount of sulfhydryl available on the surface of the foam (see FIG. 7).

In some embodiments, the polymer foam may comprise an additional polymer selected from the group consisting of polyvinyl alcohol, polyurethane, polypropylene, polystyrene, polyols, poloxamer, or a combination of one or more of these.

2. Further Modified Polymer Backbone

In some embodiments, substituted silyl-modified polymers are provided. Examples include those comprising repeat units based on polyurethane, which may be hydrophobic or hydrophilic, chitosan, crosslinked and/or uncrosslinked polyolefin, polyols, ethylene vinyl acetate (EVA), elastomers such as acrylonitrile butadiene (NBR), polychloroprene (PCP or CR), ethylene propylene rubber (EPR & EPDM), silicones, and/or fluoro carbon polymers. For example, in some embodiments, a chitosan-based polyurethane polymers or copolymers may be used. In some embodiments, the substituted silyl groups are attached to the polymer or co-polymer through an oxygen atom. In other embodiments, the substituted silyl groups are attached directly to a carbon atom of the polymer or co-polymer.

Some embodiments provide polymeric materials modified with silane molecules, containing substituted silyl groups. Examples of foam materials can include polyurethane-based foam, which may be hydrophobic or hydrophilic, including, for example a hydrocolloid-based polyurethane foam material. Other foams that may be suitable include crosslinked and/or uncrosslinked polyolefin's, polyols, ethylene vinyl acetate (EVA), and elastomers such as acrylonitrile butadiene (NBR), polychloroprene (PCP or CR), ethylene propylene rubber (EPR & EPDM), silicones, and fluoro carbon polymers. For example, in some embodiments, a polysaccharide-based polyurethane foam may be used. In some embodiments, the substituted silyl groups are attached to the foam through an oxygen atom. In other embodiments, the substituted silyl groups are attached directly to a carbon atom of the foam.

The silylated polyurethane foams disclosed herein may be made by silylating the hydroxy groups on a polymer comprising such groups. As used herein, silylation is the introduction of a substituted silyl group ($R_3Si-$) to a molecule. It involves the replacement of a hydrogen on the compound, e.g., the hydrogen of a hydroxy group, with a substituted silyl group. Without being bound by mechanism, the oxygen atom of the product, may be the same oxygen atom of the hydroxy group reactant. See "How do I apply my Silane?" Gelest Catalog. 2006, pages 19-20, which are incorporated by reference herein in their entirety.

In some embodiments, the N-hydroxysuccinimide ester (NHS ester) on one end of the Sulfo-EMCS molecule can react with the amine group of an aptamer, bioactive molecule, or polypeptide. The maleimide group on the other end of the molecule may be used to react with —SH groups provided by the sulfhydryl functionalized co-polymer or adapter. In this manner the Sulfo-EMCS may be used to link the peptide to a polymer or copolymer, including a foam. Such methods may be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is also incorporated by reference herein in its entirety. For example, other suitable amino-thio linkers may be used. These include, for example: SM(PEG)24, SM(PEG)12, SM(PEG)8, SM(PEG)6, SM(PEG)4, Sulfo-LC-SMPT, SM(PEG)2, Sulfo-KMUS, LC-SMCC, LC-SPDP, Sulfo-LC-SPDP, SMPH, Sulfo-SMPB, SMPB, SMPT, SLAB, Sulfo-SIAB, EMCS, Sulfo-SMCC, SMCC, MBS, GMBS, Sulfo-GMBS, Sulfo-MBS, SPDP, SBAP, BMPS, AMAS, and SIA.

Furthermore, the capture peptides described herein may have specially modified C-termini. For example, the C-termini may be "capped" with Cys residues bearing reactive —SH groups to facilitate the conjugation. The conjugation between an —SH reactive peptide and the —SH functionalized foam would result in a S—S bond, otherwise known as a disulfide bridge. Such reactions may be carried out, for example, under mild oxidizing conditions and at room temperature.

In some embodiments, silylated polymer will be further modified with additional adapter molecules, for example, oligopeptide oligomers or an adapter of Table 1. In some embodiments, the additional adapters are covalently attached to the backbone of the silylated-modified polymer or copolymer. In other embodiments, the adapter is covalently attached to a side chain or side group of the polymer or copolymer. In some embodiments, the additional adapter is attached via a function group (e.g., a sulfhydryl group) of a modified-polymer or copolymer, forming a material.

3. Biologically Active Components and Agents and Modified Polymer Backbone

In some embodiments, biologically active components or agents, such as a therapeutic agent, may be covalently or non-covalently attached to the polymeric material or polymer foam. The therapeutic agent may be covalently or non-covalently attached to a polymer foam comprising a polymer copolymerized with a sulfhydryl containing molecule directly or through an adapter. The therapeutic agent may be covalently attached to the polymeric material or polymer foam through an adapter and a crosslinker. The therapeutic agent may be covalently or non-covalently attached to the material or foam through methods that involve temperature, pressure, pH, radiation, light, UV light, freeze-drying, and sterilization.

In some embodiments, biologically active components or agents, including peptide-based aptamers, may be conjugated to a polymer or copolymer. Such polypeptides also referred to as "capture peptides", can be used to bind protein targets in the wound environment without inhibiting their signaling capabilities or other functions. Such capture peptides may also be used to capture and increase concentrations of biologically active proteins across a wound bed of a patient, for example, to strengthen or activate a targeted biological response.

When a peptide or a factor is attached to the sulfhydryl-functionalized dressing, it will have a dissociation constant ($K_d$), or binding affinity, that is specific to a given target molecule at a given set of conditions. In some embodiments, it may allow for reversible binding of one or more target(s). In some embodiments, the aforementioned target may be released back into a wound when used as part of the methods and devices contemplated herein. In some embodiments, ingredients may be added to the installation solution to not only help dissociate the bound factor back into the wound environment but to also interact synergistically with the retained exudate element(s) for a modulating effect so that a favorable wound healing response is elicited. Types of installation solutions are discussed in greater detail below.

Examples of instilled ingredients which may be used in some embodiments to dissociate bound molecules from the capture peptides include: saline solutions, solutions with slightly acidic pH, slightly basic pH, solutions with various surfactants (i.e. polysorbate), hypochlorite, silver nitrate, sulfur-based, biguanides, cationic, isotonic, EDTA or EGTA. In some embodiments, the fluid instilled to initiate the dissociation of the bound factors from the capture peptide will depend upon the binding strength of the factor-peptide complex, which is in turn determined by the dissociation constant. The dissociation constant may be modified by using knowledge of amino acid chemistry of the factor of interest to design a peptide/aptamer.

One example of a modified dressing or wound insert is one capable of capturing fibroblast growth factor basic via a specially designed peptide aptamer.

One example of a modified dressing or wound insert is one capable of capturing vascular endothelial growth factor via a specially designed peptide aptamer.

One example of a modified dressing or wound insert is one capable of capturing platelet derived growth factor basic via a specially designed peptide aptamer.

During the early phases of wound healing, $Ca^{2+}$ ions are typically released from the cells locally into the extracellular space. The resulting high $Ca^{2+}$ concentration is believed to be a positive effector of many cellular processes involved in wound healing such as adhesion, migration and differentiation. One example of a modified dressing or wound insert is one capable of binding a metal, such as $Ca^{2+}$, wound derived or otherwise, and retaining it at the wound site. Thus, when a high $Ca^{2+}$ concentration is required or is beneficial to the wound bed, of the dressing can be instilled or flushed with an ionic solution in order to dislodge the $Ca^{2+}$ from the dressing, into the wound bed to elicit a biological response.

Another factor is transferrin, a blood plasma protein for iron binding. Chronic wound fluid has been shown to have significantly lower transferrin levels indicating that oxidative stress occurs in chronic wounds. It is known that free iron can play a role in the formation of free radicals. Without being bound by theory, high levels of free iron may contribute to exacerbation of tissue damage and delayed wound healing. Binding and concentrating transferrin onto the dressing can be used to sequester free iron in the wound bed with subsequent release with an appropriate installation solution and subsequent removal with the exudate following the use of negative pressure. This specific time-dependent modulation of transferrin and iron levels can provide a significant benefit to the patient. In an alternate view, the affinity of transferrin for iron is very high but is reversible in that it decreases progressively with decreasing pH below neutrality. If a need for localized iron concentration is necessary, installation of a low pH solution can be used to unbind or release iron from transferrin.

Hyaluronan, or hyaluronic acid, is another possible target contemplated for use. Without being bound by theory, immobilizing and concentrating hyaluronan to the wound bed before installation with an appropriate solution for release may be used to contribute to keratinocyte proliferation and migration and reduce collagen deposition, which in turn is known to lead to reduced scarring. Hyaluronan is also known for its free-radical scavenging function that could be beneficial as it is bound to the foam on the wound site.

Lactoferrin, known for its antimicrobial and anti-inflammatory properties, is another possible target for some of the embodiments. Secreted by endothelial cells, lactoferrin has been shown to have a synergistic effect with FGF2 in that there is a marked increase in their ability together to effect fibroblast migration and proliferation. Specifically designed polypeptide aptamers can be used to bind both LF and FGF2 and release them with an appropriate installation solution in an opportune therapeutic timeframe.

TGFB-3 can be another target another possible target for some of the embodiments. This protein promotes reorganization of matrix molecules, resulting in an improved dermal architecture and reduced scarring. TGFB-3 is secreted in latent form that requires activation before it is functional. Activation of latent TGFB-3 occurs via binding to thrombospondin-1 (TSP-1). Therefore, TSP-1, may be used in some embodiments, as an ingredients in the installation fluid to modulate TGFB-3 activity.

Possible other targets include calmodulin, S-100, thyroxine and cholate receptors, amongst many others.

C. USES OF MODIFIED MATERIALS

The modified polymers described above and materials made therefrom may be used for a variety of purposes, including to (a) capture and concentrate biological targets in the wound environment, (b) specify the chemical nature of the binding, (c) to provide an electric current at the wound site (e.g., in the case of polymers with associate metal ions) and/or (d) dictate the orientation with which the target factors are presented to the cells. As discussed in greater detail in the Examples section below, modified polyurethanes, including peptide modified GranuFoam™ (GF), a type of ROCF, may be used to capture specific protein targets in vitro.

In some embodiments capture peptides linked to modified polymers may be used to bind protein targets in the wound environment without inhibiting their signaling capabilities or other functions. Such modified polymers may be used as part of a dressing or wound insert, for example, to capture and increase concentrations of biologically active proteins across a wound bed of a patient, for example, to strengthen or activate a targeted biological response.

In some embodiments, such a dressing may be used to concentrate proteins of interest such as vascular endothelial growth factor in the wound bed to trigger angiogenesis and tubule formation. Additionally, peptides may be designed to antagonize or sequester proteins that adversely affect the healing process, such as matrix metalloproteinases. Dressings made of such modified polymers may thus be used, in some embodiments, to modulate various biological pathways or to manage the presence of unwanted bioactive molecules or enzymes in the wound environment.

In some embodiments, the sulfhydryl-functionalized wound insert may be used to covalently: attach nanoparticles for distribution into the wound, conjugate sacrificial substrates for proteases or other enzymes, conjugate epitope mimetics that elicit biological responses, attach moieties that enable electrostatic attraction/repulsion of biomolecules, conjugate enzymes that retain their biological activity despite their covalent attachment. Enzymes may include kinases and phosphatases.

In addition to dressings, modified polymers, including those using sulfhydryl adapters, sulfhydryl copolymers, and polyurethane-based polymers or copolymers, may also be used in a wide array of other materials, matrixes and biomedical devices, including catheters. In such embodiments, they may be used to conjugate a variety of biologically active components, including antimicrobial compounds. The application of these materials to a negative pressure-based therapy is discussed in greater detail below.

Materials described herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

It should be recognized that the particular anion or cation forming a part of any salt is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

D. PREPARATION OF INSERTS COMPRISING FOAM MATERIALS BASED

In another aspect, foam-based polymers may be physically and/or chemically treated, coated or manipulated before or after they are covalently linked to an active component. Some embodiments of making modified wound inserts comprise: compressing (and/or felting) at least a portion of a foam. Some embodiments comprise: treating (e.g., by applying heat, or activating a coating that has been applied to) the compressed foam such that the foam remains substantially compressed in the absence of an external compressive force. For example, in some embodiments, treating comprises heating the foam (e.g., foam) to an elevated temperature sufficient to reduce resiliency of the foam. For example, the foam can be heated to a temperature at which resiliency of the foam is reduced and/or relaxed, but that is below the melting temperature of the foam (e.g., such that the foam is not degraded by the elevated temperature). In this way, the foam can be compression set using heat and pressure (compressive force) to relax compressive strains developed in the foam. Generally, high temperatures are used to achieve the compression set. To achieve the desired "set" such that resiliency of the foam is reduced and/or the foam remains substantially compressed in the absence of a compressive force, temperatures can range from 158 degrees Fahrenheit to 482 degrees Fahrenheit (e.g., equal to, less than, greater than, or between any of: 140, 160, 180, 200, 220, 240, 260, 280, 300, 320, 340, 360, 380, 400, 420, 440, 460, 480, 500 degrees Fahrenheit, depending upon the particular foam used). The foam may also be put through a cooling cycle to help retain the set introduced. For example, the foam may be cooled to a temperature below room or ambient temperature (e.g., to or in a temperature equal to, less than, greater than, or between any of: 0, 5, 10, 15, 20, 25, 30, 35, 40, 45, 50, 55, 60, 65, or 70 degrees Fahrenheit). In some embodiments of the present methods of forming a modified wound insert, the foam is disposed between two heated plates or platens (e.g., in a plate or platen press and/or where the plates are heated to a temperature sufficient to reduce the resiliency of the foam); and the press is actuated to move the plates toward one another (e.g., perpendicular to thickness 320 of thick portions 304) such that the foam is compressed to the desired overall thickness or degree of compression). Such a press can be electrically, mechanically, and/or hydraulically operated.

Some embodiments of the present methods of making modified wound inserts also comprise: cooling the foam (e.g., after heating the foam) such that the compressed portion of the foam remains substantially compressed at room temperature (e.g., at a temperature of 72 degrees Fahrenheit) in the absence of a compressive force. In other embodiments, cooling the foam includes cooling a coating that has been applied to the foam such that the compressed portion remains substantially compressed in the absence of a compressive force at a temperature or temperature range equal to, less than, greater than, or between any of: 10, 20, 30, 40, 50, 60, 70, 80, 90, 100, 110, 120, 130, 140, and/or 150 degrees Fahrenheit.

Thick and thin regions in the foam can be formed by any suitable methods, such as, for example, laser cutting or the like. Such methods are taught, for example, by U.S. Patent Application Publication 2011/0178451, which is incorporated herein by reference.

In such embodiments, the coating can be dispersed through the foam, such as, for example, by spraying the foam with the coating, dipping the foam in the coating, and/or any other suitable way of dispersing the coating in the foam. In some embodiments, for example, the foam can be coated with a material that has a transition temperature (e.g., melting point, glass transition, etc.) that occurs at a relatively low temperature (e.g., lower than the foam alone), or that develops stiffness as it dries. In some embodiments, the coating can be configured to enable the foam to be compressed (and/or compression set) at lower temperatures (e.g., without heating), such that the coating becomes stiff or otherwise resistant to expansion as it cools or dries to hold the foam in its compressed configuration. For example, a fluid adhesive may be applied to thick portions before compressing the foam and permitted to dry before removing the compressive force, such that the dried adhesive will resist expansion from the compressed thickness. In other embodiments, the coating can be configured to compression set the foam such that the compression is reversible (e.g., at least partially and/or completely reversible) such that the foam can expand (e.g., after placing in or on a wound) as it warms or absorbs water. In some embodiments, the coating comprises a cross-linkable polymer and/or activating comprises exposing the coating to light and/or elevated temperature (e.g., above ambient temperature, such as, for example, a temperature sufficient to cause at least part of the cross-linkable polymer to cross-link) to cause at least some portion of the cross-linkable polymer to become modified.

Examples of suitable coatings include cross-linkable polymers that contain n-methylol acrylamide (NMA). NMA is a monomer that may be co-polymerized with many other monomers (such as acrylics & vinyls). On heating, (e.g., to about 140° C.), NMA reacts with itself and other hydroxyl-containing groups (e.g., carboxyl). Similarly, urea formaldehyde, melamine formaldehyde, and/or phenol formaldehyde can be caused to react with themselves and other hydroxyl-containing polymers to form crosslinks. Other crosslinking agents may include, for example, modified ethylene ureas, which react with hydroxyl-containing polymers at elevated temperatures to crosslink them. Other crosslinking agents can include peroxides which will crosslink most polymers at elevated temperatures. Polymers containing hydroxyl and carboxyl groups may also be combined, and, when heated, may form polyester crosslinks. Additionally, epoxy prepolymers can be used that have low reactivity at room temperatures, and when heated, react quickly to form an epoxy polymer with crosslinks. Similarly, polymeric isocyanates may be used that will only react significantly fast at elevated temperatures and in presence of hydroxyl groups, amines, or moisture to form polyurethanes or polyureas.

In some embodiments, a combination of high-density regions and low-density regions cooperate to provide various characteristics for the present modified wound inserts. For example, the high-density regions have a smaller aggregate cell size and increased cell density, such that the high-density regions have improved wicking function and more-effectively transmit fluid (e.g., draw fluids away from the wound surface and/or communicate fluid from a fluid source to the wound surface more effectively than the low-density regions. The high-density regions are generally also mechanically stronger than the low-density regions, such that the high-density regions can provide structural support for the low-density regions and/or the modified wound insert as a whole (e.g., such that the modified wound insert is resistant to tearing in directions that are not parallel to the low-density regions). Additionally, the low-density regions have a larger effective cell or pore size such that the low-density regions are less-susceptible to clogging. Especially when a negative pressure is applied to draw fluid and/or exudate away from the wound and through the modified wound insert, the larger pore size of the low-density regions may permit fluids to be drawn through the low-density regions at a higher velocity than the fluid is drawn through the high-density regions, such that particulate and granular matter are drawn to and/or through the low-density to discourage and/or decrease the likelihood of clogging in the high-density regions. In some embodiments, the foam can also be coated with a hydrophilic material to improve wicking properties of the modified wound insert.

The low-density regions may also be configured to permit the wound dressing to bend and/or otherwise conform to a wound. For example, the low-density regions can be relatively easier to bend (and/or less resilient when the modified wound insert is bent or folded along a low-density region) such as to double over a modified wound insert, and/or to conform a modified wound insert to additional hardware such as plates, pins, or the like.

Typical single-density foam modified wound inserts are isotropic such that under negative pressure, a typical single-density foam modified wound insert will contract proportionally in all directions. In some embodiments, the present modified wound inserts may also be configured to be anisotropic, such that the present modified wound inserts can be configured to mechanically assist with wound closure. For example, low-density regions are less-dense (and will compress more under negative pressure) than high-density regions. As such, if negative pressure is applied to modified wound insert, low density regions will contract more than high-density regions, such that high-density regions will be drawn together and modified wound insert will contract laterally more than longitudinally. In other embodiments, the present modified wound inserts can be configured to have alternating and sequentially larger closed ring-shaped high-density regions and low-density regions, such that under negative pressure, the modified wound insert will contract laterally inward to its own center.

In some embodiments, thick portions, thin portions, high-density regions, and/or low-density regions can be coated and/or printed (either before or after compression) to enhance the hydrophilic or hydrophobic properties of individual regions of the foam or of the foam as a whole. Such coated regions may also contain and/or be coated with other additives, such as antibiotics, or blockage-reducing agents.

In some embodiments, wound dressings comprise a wound dressing configured to be positioned on a wound (e.g., 26 of FIG. 4) of a patient (e.g., 30) and/or on or in contact with the wound surface (e.g., 42).

The wound dressings described herein comprising a sulfhydryl-functionalized polymer foam may further comprise a backing, such as a drape, covering the polymer foam substrate. The drape may be occlusive and may extend beyond the polymer foam substrate. The drape may include an adhesive portion. The adhesive portion of the backing may extend over the polymer foam for adhering the wound dressing directly to the area around the wound site. The wound dressing may include an absorbant layer between the polymer foam and the drape.

Some embodiments of the present wound-treatment methods comprise: positioning a modified wound insert (e.g., any of the present modified wound inserts such as 34) on a wound (e.g., 26) of a patient (e.g., 30), where the modified wound insert comprises a foam (e.g., 116). In some embodiments, the foam is sterile (e.g., substantially free of microbes and/or bacteria). Some embodiments further comprise: coupling a drape (e.g., 38) to skin (e.g., 46) adjacent the wound such that the drape covers the modified wound insert and the wound, and forms a space between the drape and the wound. Some embodiments comprise: applying negative pressure to the wound through the wound dressing (e.g., through the modified wound insert). In some embodiments, applying negative pressure to the wound comprises activating a vacuum source (e.g., apparatus 14 of FIG. 4, or vacuum source 200 of FIG. 6) that is coupled to the wound dressing. Some embodiments comprise: delivering a fluid to the wound through the wound dressing. In some embodiments, delivering a fluid comprises activating a fluid source (e.g., fluid source 248 of FIG. 6) that is coupled to the wound dressing.

In other embodiments, the sulfhydryl-modified copolymer may be conjugated to another dressing or medical device, in order to convey therapeutic functionality to that device. In this form, the sulfhydryl modified material may be a foam, a sheet, membrane, bead, or other device, which may be covalently attached to a given medical device through means of physical or chemical bonding. In this embodiment, the sulfhydryl-modified copolymer carries or influences the therapeutic agent, and by virtue of conjugation, conveys that therapeutic mechanism to the device that it conjugates.

Some embodiments of the present wound-treatment systems comprise either embodiment of system 10 (or any subset of components of either embodiment of system 10), and one or more of the present modified wound inserts and/or wound dressings.

The various illustrative embodiments of devices, systems, and methods described herein are not intended to be limited to the particular forms disclosed. Rather, they include all modifications and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

It will be understood that the benefits and advantages described above may relate to one embodiment or may relate to several embodiments. It will further be understood that reference to 'an' item refers to one or more of those items, unless otherwise specified.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the scope of the present disclosure.

E. DEVICES COMPRISING AN MODIFIED WOUND INSERT

The modified polymers described above and materials made therefrom may be used for a variety of purposes, including to (a) capture and concentrate biological targets in the wound environment, with the option to release back into the wound bed, (b) specify the chemical nature of the binding, and/or (c) dictate the orientation with which the target factors are presented to the cells.

A dressing or wound insert made for a modified polymer may be used together with negative pressure wound therapy. In some embodiments, compatible foam coated with aptamers or small capture peptides (ligands) which select for beneficial molecules in the wound fluid as it passes through the foam would thereby prevent their removal into the negative pressure wound therapy canister. Aptamers may include small molecules, nanoparticles, oligomers, pharmaceuticals, peptides, biotin, avidin, ligands, dendrimers, arborols, and others. Appropriate molecules for selection from wound fluid include metabolites, growth factors, chemokines, cytokines, proteins, polypeptides, cofactors, neurotransmitters, inflammatory mediators, hormones, bacteria, and small molecules, which would not impede fluid flow through the negative pressure wound therapy dressing. In some embodiments, appropriate adapters and/or capture peptides would bind the wound fluid molecules in such an orientation that the "active site" of the wound fluid molecule is still available for eliciting a biological response. For example, one such molecule may be VEGF. VEGF has specific sites on the molecule that bind to cellular receptors. The binding of the VEGF molecule to the cellular receptor may be used to initiate a biological response, typically angiogenesis.

In some embodiments, the methods taught herein may be used to bind to molecules chemotactic to macrophages such as MCP1, which may be used to stimulate macrophage migration into the wound and thereby progress the wound from a chronic to a healing state. In some embodiments, PDGF or collagen fragments could be bound during the proliferative or late inflammatory phases to stimulate the migration of fibroblasts into the wound. Stimulating the migration of macrophages and then fibroblasts into the wound may assist in the progression of the wound through the inflammatory phase and into the proliferative phase of wound healing. In some embodiments, Nitric Oxide Synthase could be bound from the wound fluid to stimulate perfusion. This may help to promote healing by allowing a higher level of nutrients into the wound. In some embodiments, anti-inflammatory cytokines such as IL4 or IL10 could be bound to decrease inflammation, thus progressing the wound more quickly through the inflammatory and into the proliferative phase of healing. DNA fragments could also be bound to the dressing. In some embodiments, the binding of highly charged DNA could enable current to be passed through the dressing. Electrical stimulation has been used for many years in the treatment of wounds. Therefore, binding DNA to the wound dressing may allow for the application of current to the wound.

Figure 4:
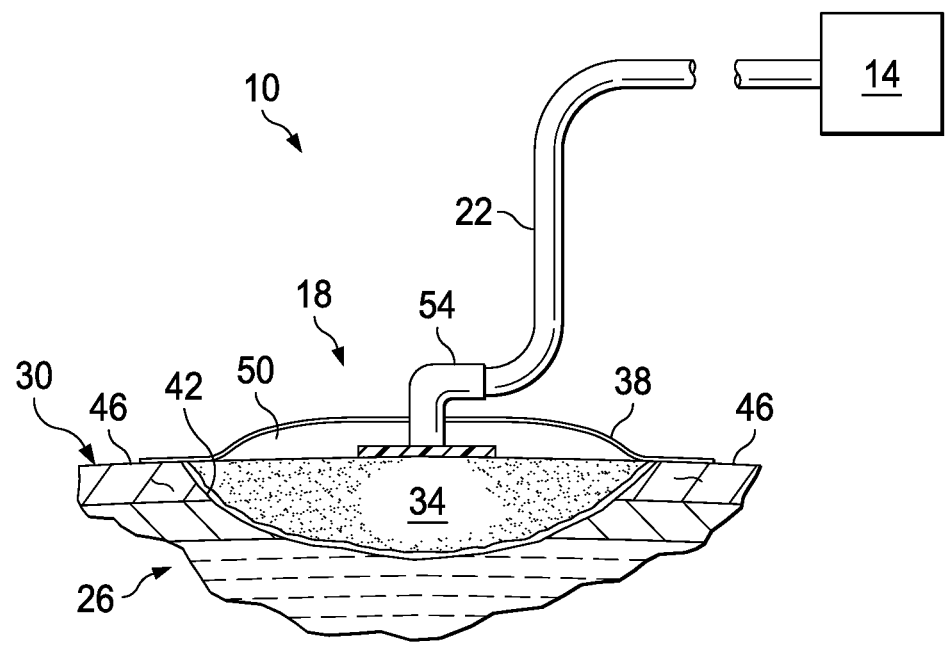
FIG. 4 depicts a side view of one embodiment of a wound dressings of the embodiments having one of the present modified wound inserts and coupled to a wound site and to a wound treatment apparatus.

Referring now to the drawings, and more particularly to FIG. 4, shown therein is an embodiment of one of the present wound treatment system 10. In the embodiment shown, apparatus 10 comprises a wound-treatment apparatus 14, and a wound dressing 18 coupled to apparatus 14 by a conduit 22. As shown, dressing 18 is configured to be coupled to (and is shown coupled to) a wound 26 of a patient 30. More particularly, in the embodiment shown, dressing 18 comprises a modified wound insert 34 and a drape 38. As shown, modified wound insert 34 is configured to be positioned (and is shown positioned) on wound 26 (e.g., on or adjacent to wound surface 42), and/or drape 38 is configured to be coupled to (and is shown coupled to) skin 46 of the patient adjacent to wound 26 such that drape 38 covers modified wound insert 34 and wound 26, and forms a space 50 between drape 38 and wound 26 (e.g., wound surface 42).

Apparatus 14 can comprise, for example, a vacuum source configured to be actuatable (and/or actuated) to apply negative pressure (e.g., via conduit 22) to wound dressing 18, a fluid source configured to be actuatable (and/or actuated) to deliver (e.g., via conduit 22) a fluid (e.g., an installation fluid such as a medicinal fluid, antibacterial fluid, irrigation fluid, and or the like) to wound dressing 18. System 10 can be implemented and/or actuated and/or coupled to patient 30 in any of various configurations and/or methods similar to those described in the prior art. For example, various wound therapy systems and components are commercially available through and/or from KCI USA, Inc. of San Antonio, Tex., U.S.A., and/or its subsidiary and related companies (collectively, "KCI").

Conduit 22 can comprise a single lumen conduit (e.g., switched between a vacuum source and/or a fluid source and apparatus 14), or can comprise multiple single-lumen conduits or a multi-lumen conduit such that, for example, fluid can be delivered and/or negative pressure can be applied to wound dressing 18 individually and/or simultaneously. Additionally, conduit 22 can comprise, for example, a first lumen for the application of negative pressure and/or fluid delivery, and at least one additional lumen for coupling to pressure sensor(s) to sense pressure or negative pressure between drape 38 and surface 42. In some embodiments, conduit 22 can comprise multiple lumens (e.g., as in a single conduit with a central lumen for application of negative pressure and/or fluid delivery, and one or more peripheral lumens disposed adjacent or around the central lumen such that the peripheral lumens can be coupled to a pressure sensor to sense a pressure or negative pressure between drape 38 and surface 42 (e.g. in space 50). The lumens may be arranged with a central lumen and other lumens disposed radially around the central lumen, or in other suitable arrangements. The lumens may also be provided in separate conduits. In the embodiment shown, system 10 further comprises a wound dressing connection pad 54 configured to be coupled (and is shown coupled) to conduit 22. One example of a suitable connection pad 54 is the "V.A.C. T.R.A.C.® Pad," commercially available from KCI. One example of a suitable drape 38 includes the "V.A.C.® Drape" commercially available from KCI.

Figure 5:
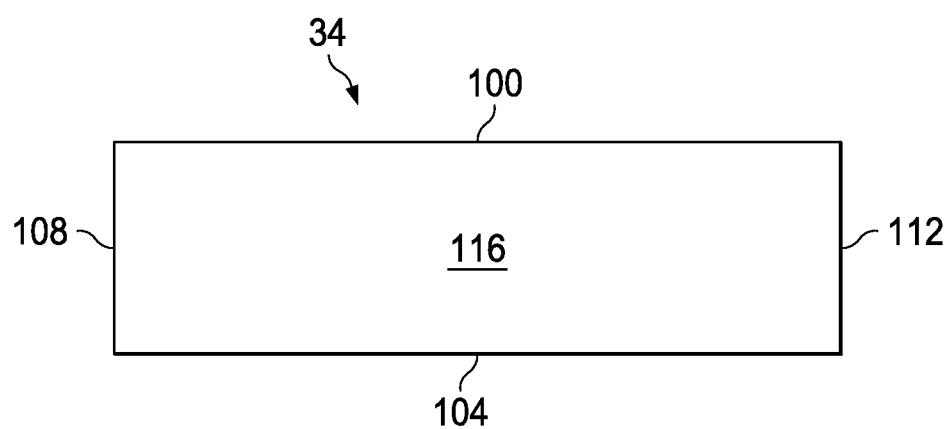
FIG. 5 depicts an enlarged side view of the modified wound insert of FIG. 4.

Referring now to FIG. 5, a side view of a modified wound insert 34 is shown. Modified wound insert 34 has an upper side 100, a lower side 104, lateral sides 108, 112 and interior volume 116. Although only one side is shown of modified wound insert 34, it will be understood by those of ordinary skill in the art that modified wound insert 34 includes a three-dimensional rectangular volume having a depth extending perpendicular to the side shown. In other embodiments, modified wound insert 34 can have any suitable shape, such as, for example, a round cylindrical shape, a fanciful shape, or may be trimmed to fit an irregular shape of a wound (e.g., 26 and/or wound surface 42). Modified wound insert 34 can comprise a foam, such as, for example, open-celled foam (which may also be reticulated).

Embodiments of the present wound treatment methods may be better understood with reference to FIG. 4, which depicts a schematic block diagram of one embodiment of system 10. In the embodiment shown, wound dressing 18 is coupled to apparatus 14, and apparatus 14 comprises a vacuum source 200 (e.g., a vacuum pump and/or the like) coupled to a canister 204 (e.g., configured to receive exudate and or the like from wound dressing 18) by way of a conduit 208. In the embodiment shown, apparatus 14 further comprises: a pressure sensor 212 having a first pressure transducer 216 coupled to conduit 208 by way of conduit 220 and/or tee-fitting 224, and a second pressure transducer 228 coupled to canister 204 and/or wound dressing 18 by way of conduit 232. Pressure sensor 212 is configured to sense the negative pressure in wound dressing 18, and/or any of the various lumens (e.g., within conduits) coupled to wound dressing 18, pressure sensor 212, and/or vacuum source 200.

In the embodiment shown, apparatus 14 further comprises a pressure release valve 236 coupled to conduit 232. Further, in the embodiment shown, canister 204 and vacuum source 200 are coupled to wound dressing 18 by way of conduit 240; and/or canister 204 can comprise a filter 244 at or near an outlet of canister 204 to prevent liquid or solid particles from entering conduit 208. Filter 244 can comprise, for example, a bacterial filter that is hydrophobic and/or lipophilic such that aqueous and/or oily liquids will bead on the surface of the filter. Apparatus 14 is typically configured such that, during operation, vacuum source 200 will provide sufficient airflow through a filter 244 that the pressure drop across filter 244 is not substantial (e.g., such that the pressure drop will not substantially interfere with the application of negative pressure from wound dressing 18 from vacuum source 200).

In the embodiment shown, apparatus 14 further comprises a fluid source 248 coupled to wound dressing 18 by way of a conduit 252 that is coupled to conduit 240 such as, for example, by way of a tee- or other suitable fitting 256. In some embodiments, tee fitting 256 can comprise a switch valve and/or the like such that communication can be selectively permitted between wound dressing 18 and vacuum source 200, or between wound dressing 18 and fluid source 248. In some embodiments apparatus 14 comprises only one of vacuum source 200 and fluid source 248. In embodiments of apparatus 14 that comprise only fluid source 248, canister 204 and/or pressure sensor 212 can also be omitted. In various embodiments, such as the one shown, conduit 232 and/or conduit 240 and/or conduit 252 can be combined and/or comprised in a single multi-lumen conduit, such as is described above with reference to FIG. 4. In some embodiments, fluid source 248 is coupled directly to wound dressing 18 (e.g., conduit 252 is coupled one end to wound dressing 18, such as via connection pad 54, and conduit 252 is coupled on the other end to fluid source 248; and conduit 252 is not coupled to tee fitting 256).

Figure 6:
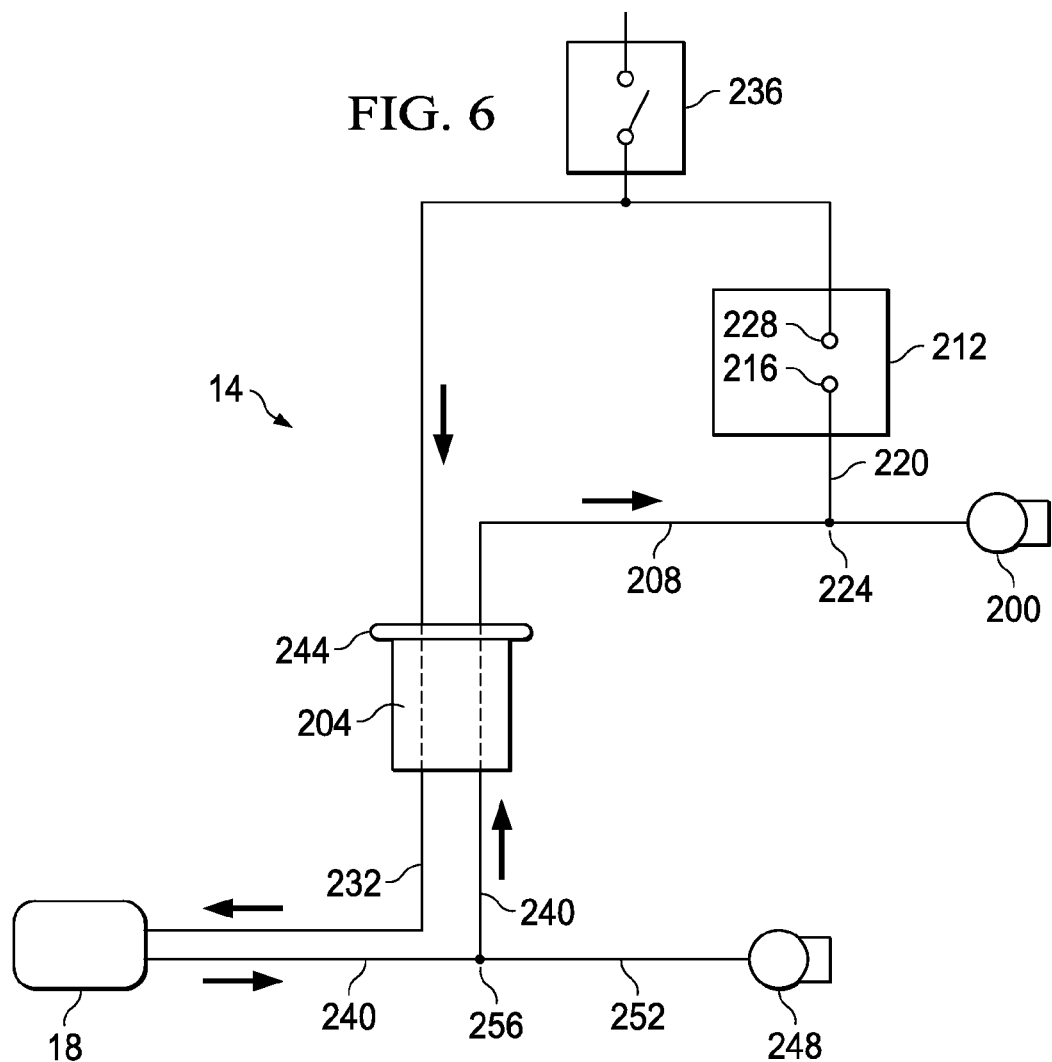
FIG. 6 depicts a schematic block diagram of one embodiment of a wound treatment apparatus that can comprise and/or be coupled to and/or be used with the present wound dressings and/or modified wound inserts.

In various embodiments, such as the one shown in FIG. 6, apparatus 14 can be configured such that as soon as liquid in the canister reaches a level where filter 244 is occluded, a much-increased negative (or subatmospheric) pressure occurs in conduit 208 and is sensed by transducer 216. Transducer 216 can be connected to circuitry that interprets such a pressure change as a filled canister and signals this by means of a message on an LCD and/or buzzer that canister 204 requires emptying and/or replacement, and/or that automatically shuts off or disables vacuum source 200.

Apparatus 14 can also be configured to apply negative (or subatmospheric) pressure (e.g., continuously, intermittently, and/or periodically) to the wound site, and/or such that pressure relief valve 236 enables pressure at the wound site to be brought to atmospheric pressure rapidly. Thus, if apparatus 14 is programmed, for example, to relieve pressure at ten-minute intervals, at these intervals pressure relief valve 236 can open for a specified period, allow the pressure to equalize at the wound site, and then close to restore the negative pressure. It will be appreciated that when constant negative pressure is being applied to the wound site, valve 236 remains closed to prevent leakage to or from the atmosphere. In this state, it is possible to maintain negative pressure at the wound site without running and/or operating pump 200 continuously, but only from time to time or periodically, to maintain a desired level of negative pressure (i.e. a desired pressure below atmospheric pressure), which is sensed by transducer 216. This saves power and enables the appliance to operate for long periods on its battery power supply.

In some embodiments, factors may be removed, or their concentration modulated, using electrical pulses, light, ultrasound and temperature.

F. INSTILLATION SOLUTIONS

In some embodiments dressing made from the modified polymers disclosed herein may be used together with wound instillation solutions, for example in the application of a negative pressure treatment to a patient's wound. In some embodiments, the instillation solution comprises ingredients to help release or modulate the release of the factors bound to the foam.

Examples of instilled ingredients which may be used in some embodiments to dissociate bound molecules include: saline solutions, solutions with slightly acidic pH, solutions with slightly basic pH, solutions with various surfactants (i.e. polysorbate), and solutions with slight ionic charge, EDTA or EGTA. In some embodiments, the fluid instilled to initiate the dissociation of the bound factors from the capture peptide will depend upon the binding strength of the factor-capture peptide complex, which is in turn determined by the dissociation constant.

In some embodiments, the instillation solution comprises hypochlorous acid (HOCl) and hypochlorite ion. Both are examples of effective antimicrobial agents for biocidal action. For example, HOCl is typically capable of killing a broad spectrum of microbes (e.g., bacteria, viruses, fungus, yeast, and the like); often in a relatively short period of time (e.g., is capable of killing greater than 99% of microbes within a period of less than 10 seconds). Such antimicrobial agents can be generated or formed by a combination of the present reactive agents and fluid (e.g., water and/or aqueous solution, such as, for example, saline solution) and may be more effective and/or more versatile than antibiotics and other commonly used antimicrobial agents used in wound treatment in the past. For example, antibiotics may be bacteria-specific such that testing may be required to determine a suitable antibiotic to use for a specific wound or infection; and/or such that antibiotics may have only limited effectiveness for individual wounds and/or infections (e.g., where testing is not performed and/or where a wound is infected with a plurality of different bacteria). Such testing may take as long as several days to determine an appropriate antibiotic, delaying treatment or selection of an effective antibiotic. Additionally, bacteria may develop resistance to antibiotics, such that antibiotics may have reduced effectiveness after an amount of time. Further, antibiotics are typically administered intravenously (systemically) such that antibiotics may kill beneficial bacteria (e.g., in a patient's digestive system) and/or may cause organ damage (e.g., to a patient's liver).

In contrast, the reactive agents (and/or antimicrobial products of the reactive agents) of the present embodiments can be configured to have a broad-spectrum killing power that will kill a variety of microbes (e.g., fungus, bacteria, viruses, fungus, yeast, etc.). Additionally, the present reactive agents (and/or antimicrobial products of the reactive agents) can be delivered locally (preventing systemic damage or other side effects to organs and the like).

However, due to the reactivity of HOCl or OCl⁻ with oxidizable organic substances, its utility in wound care applications has previously been limited. For example, prior art methods of generating hypochlorous acid have required electrolysis of saltwater or the like (e.g., with expensive equipment at a patient's bedside). By way of another example, commercially available chemicals (e.g., bleach) have a hypochlorous acid concentration of 5% or greater, which is too high to permit medical uses (e.g., will cause cytoxicity). Additionally, at suitable medical concentrations (e.g., 2-20 mM hypochlorous acid solutions), approximately 99% or more of the solution is water, such that shipping is more expensive and/or more difficult than necessary. Further, storage of hypochlorous acid solutions is difficult, as reactions with containers typically degrade or reduce the concentration of the hypochlorous acid solution. However, the present wound inserts can be deposited with reactive agents (have reactive agents deposited in the foam of the wound inserts) such that upon application of a fluid such as saline or water, OCl (and/or ClO⁻) is released (e.g., to form hypochlorous acid) and delivered to a wound for biocidal action.

G. EXAMPLES

The following examples are included to demonstrate preferred embodiments. It should be appreciated by those of skill in the art that the techniques disclosed in the examples which follow represent techniques discovered by the inventor to function well in the practice of the products, compositions, and methods described herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Preparation of Sulfhydryl Functionalized Foam

Figure 7:
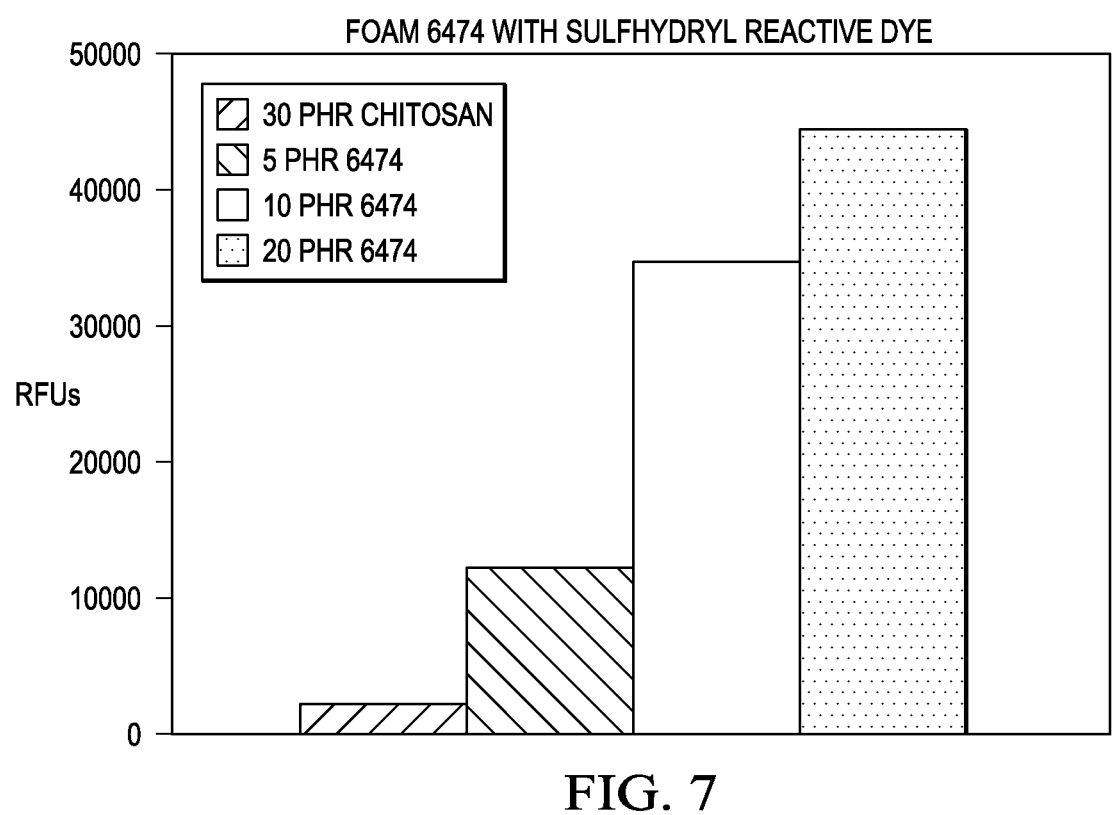
FIG. 7 depicts a graph showing the relative fluoresce (RFU) of sulfhydryl test foams. From left to right bars in the graph indicate fluorescence for foams incorporating 30 chitosan components per hundred resin (phr) as a negative control or 5 phr, 10 phr or 20 phr (3-Mercaptopropyl) methyldimethoxysilane, which provides a free sulfhydryl group.

Foams were made by copolymerizing a sulfhydryl containing molecule into polyurethane foam. The molecule was polymerized in a way that leaves the sulfhydryl group available for chemical reactions. The resulting covalently integrated sulfhydryl groups provide a way to engineer the foam with disulfide bridges and other linkages for biomolecule attachment. For foam 6474, isocyanate, polyol, and various amounts of a sulfhydryl—containing molecule (3-Mercaptopropyl) methyldimethoxysilane were copolymerized along with surfactants. To assess the effectiveness of the sulfhydryl adapter/copolymer incorporation, the foams were visualized with a sulfhydryl reactive dye. Results of these studies are shown in FIG. 7 and Table 2 below and demonstrated effective incorporation of the molecules into the foam and a dose dependent increase in fluorescence of the foams.

TABLE 2

Fluorescence assay of sulfhydryl test foams

| Well ID | Name | Well | Mean RFU [390, 420] | Count | Mean | Std Dev | CV (%) |
|---|---|---|---|---|---|---|---|
| SPL1 | 30 phr chitosan | A1 | 2107 | 2 | 2385 | 394 | 16.5 |
| | | B1 | 2664 | | | | |
| SPL2 | 5 phr 6474 | A2 | 12815 | 2 | 11720 | 1548 | 13.2 |
| | | B2 | 10626 | | | | |
| SPL3 | 10 phr 6474 | A3 | 34616 | 2 | 35068 | 639 | 1.82 |
| | | B3 | 35521 | | | | |
| SPL4 | 20 phr 6474 | A4 | 42787 | 2 | 44632 | 2609 | 5.85 |
| | | B4 | 46478 | | | | | phr = parts per hundred resin;
RFU = relative fluorescence units

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

What is claimed is:

1. An open cell foam comprising a sulfhydryl-functional polyurethane polymer comprising a sulfhydryl group available for chemical reaction wherein the sulfhydryl group is provided by an adapter covalently attached to the polyurethane polymer, wherein the adapter has the structure of formula (I):

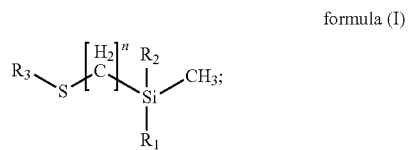

formula (I)

wherein one or both of R1 and R2 forms a first covalent bond with the material and the other is OH, OCH3, O(CH2)1-4)CH3, or a covalent bond with the polymer; n is 1-30; and $R_3$ is H, further comprising a biologically active agent covalently attached to the sulfhydryl group or through a disulfide group derived from the sulfhydryl group.

2. The open cell foam of claim 1, further comprising a crosslinker covalently attached to the adapter.

3. The open cell foam of claim 2, further comprising a biologically active agent covalently attached to the crosslinker.

4. The open cell foam of claim 1, wherein the biologically active agent is a therapeutic agent selected from the group consisting of a peptide, polypeptide, peptide matrix, protein matrix, carbohydrate, oligonucleotide, antimicrobial, small molecule, nanoparticle, nanobot, aliphatic hydrocarbon chain, surfactants, alginate, aptamer, and a combination thereof.

5. The open cell foam of claim 1, wherein the biologically active agent comprises a metal cation in the +1, or +2 state.

6. The open cell foam of claim 1, wherein the biologically active agent is a therapeutic agent selected from the group consisting of a peptide, polypeptide, peptide matrix, protein matrix, carbohydrate, oligonucleotide, antimicrobial, small molecule, nanoparticle, nanobot, aliphatic hydrocarbon chain, surfactants, alginate, aptamer, and a combination thereof.

7. The open cell foam of claim 2, wherein the biologically active agent is a therapeutic agent selected from the group consisting of a peptide, polypeptide, peptide matrix, protein matrix, carbohydrate, oligonucleotide, antimicrobial, small molecule, nanoparticle, nanobot, aliphatic hydrocarbon chain, surfactants, alginate, aptamer, and a combination thereof.

8. A wound dressing comprising the foam of claim 1.

9. A method for treating a wound comprising contacting a wound site with a wound dressing of claim 1.

10. The method of claim 9, wherein the method further comprises applying negative pressure to the wound site.

11. The method of claim 10, wherein the method further comprises applying wound instillation solution to the wound site.

12. The method of claim 11, wherein the instillation solution includes one or more agents that modulate the release of the biologically active agent.

* * * * *